US009029558B2

(12) United States Patent
Osaka et al.

(10) Patent No.: US 9,029,558 B2
(45) Date of Patent: May 12, 2015

(54) CARBAZOLE COMPOUND, LIGHT-EMITTING ELEMENT, LIGHT-EMITTING DEVICE, ELECTRONIC DEVICE, AND LIGHTING DEVICE

(75) Inventors: Harue Osaka, Kanagawa (JP); Nobuharu Ohsawa, Tochigi (JP); Masato Suzuki, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 54 days.

(21) Appl. No.: 13/570,367

(22) Filed: Aug. 9, 2012

(65) Prior Publication Data
US 2013/0204003 A1 Aug. 8, 2013

(30) Foreign Application Priority Data

Aug. 18, 2011 (JP) ................................. 2011-178966
Jun. 15, 2012 (JP) ................................. 2012-135953

(51) Int. Cl.
*C07D 401/14* (2006.01)
*H01L 51/00* (2006.01)

(52) U.S. Cl.
CPC ......... *H01L 51/0072* (2013.01); *H01L 51/0067* (2013.01); *H01L 51/0085* (2013.01); *C07D 401/14* (2013.01)

(58) Field of Classification Search
CPC .................................................... C07D 401/04
USPC ..................................................... 546/276.7
See application file for complete search history.

(56) References Cited

U.S. PATENT DOCUMENTS

| 7,504,162 | B2 | 3/2009 | Nomura et al. |
| 7,641,986 | B2 | 1/2010 | Lo et al. |
| 7,740,954 | B2 | 6/2010 | Burn et al. |
| 8,025,988 | B2 | 9/2011 | Burn et al. |
| 2003/0205696 | A1 | 11/2003 | Thoms et al. |
| 2012/0302762 | A1 | 11/2012 | Osaka et al. |
| 2012/0330025 | A1 | 12/2012 | Osaka et al. |
| 2013/0292659 | A1* | 11/2013 | Kim et al. ........................ 257/40 |

FOREIGN PATENT DOCUMENTS

| JP | 08-003547 | 1/1996 |
| JP | 10-226785 | 8/1998 |
| JP | 2001-244077 | 9/2001 |
| JP | 2001-257076 | 9/2001 |
| JP | 2002-100480 | 4/2002 |
| JP | 2003-133075 | 5/2003 |
| JP | 2003-267976 | 9/2003 |
| JP | 2003-317966 | 11/2003 |
| JP | 2004-018787 | 1/2004 |
| JP | 2005-521210 | 7/2005 |
| JP | 2009-227604 | 10/2009 |
| KR | 2012-059815 | * 6/2012 |
| WO | WO 03/007973 A1 | 9/2003 |
| WO | WO-03/079736 A1 | 9/2003 |
| WO | WO 2004/101517 A1 | 11/2004 |

OTHER PUBLICATIONS

Hameurlaine.A et al., "Synthesis of Soluble Oligocarbazole Derivatives,", Tetrahedron Letters, Jan. 27, 2003, vol. 44, No. 5, pp. 957-959.
Zhang.Q et al., "Carbazole-Based Hole-Transporting Materials for Electroluminescent Devices,", Synthetic Metals, 2003, vol. 137, No. 1-3, pp. 1111-1112.
McClenaghan.N. et al., "Ruthenium(II) Dendrimers Containing Carbazole-Based Chromophores as Branches,", J. Am. Chem. Soc. (Journal of the American Chemical Society), Apr. 10, 2003, vol. 125, No. 18, pp. 5356-5365.

(Continued)

*Primary Examiner* — Patricia L Morris
(74) *Attorney, Agent, or Firm* — Nixon Peabody LLP; Jeffrey L. Costellia

(57) ABSTRACT

A novel carbazole compound is provided which can be used as a host material for a light-emitting substance (substance emitting fluorescence or substance emitting phosphorescence). A light-emitting element with high emission efficiency, and a light-emitting device, an electronic device, or a lighting device which has low power consumption are provided. A carbazole compound represented by General Formula (G1) below.

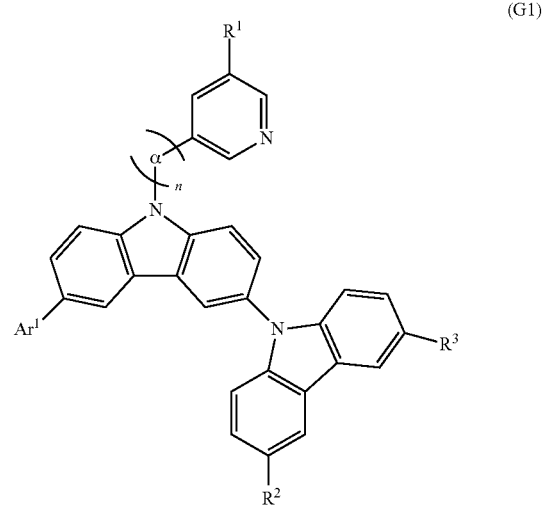

(In the formula, $Ar^1$ represents any of hydrogen, a substituted or unsubstituted phenyl group, and a carbazolyl group; $R^1$ to $R^3$ each independently represent any of hydrogen, a substituted or unsubstituted phenyl group, and a substituted or unsubstituted biphenyl group; $\alpha$ represents any of a substituted or unsubstituted phenylene group and a substituted or unsubstituted biphenylene group; and n is any of 0, 1, and 2.)

3 Claims, 20 Drawing Sheets

(56) References Cited

OTHER PUBLICATIONS

Grigalevicius.S et al., "Photoconductive Molecular Glasses Consisting of Twin Molecules,", J. Photochem. Photobiol. A: Chem. (Journal of Photochemistry and Photobiology A: Chemistry), Jan. 24, 2003, vol. 154, No. 2-3, pp. 161-167.

Grigalevicius.S et al., "Synthesis and Properties of Poly(3,9-Carbazole) and Low-Molar-Mass Glass-Forming Carbazole Compounds,", Polymer, Apr. 1, 2002, vol. 43, No. 9, pp. 2603-2608.

Grigalevicius.S et al., "Hole-Transporting Molecular Glasses Based on Carbazole and Diphenylamine Moieties,", Materials Chemistry and Physics, Dec. 1, 2001, vol. 72, No. 3, pp. 395-400.

Kundu,P et al., "High-Tg Carbazole Derivatives as Blue-Emitting Hole-Transporting Materials for Electroluminescent Devices,", Adv. Funct. Mater. (Advanced Functional Materials), Jun. 1, 2003, vol. 13, No. 6, pp. 445-452.

Kimoto.A et al., "Synthesis of Novel Carbazole Dendrimers Having a Metal Coordination Site,", Chemistry Letters, Aug. 1, 2003, vol. 32, No. 8, pp. 674-675, The Chemical Society of Japan.

Kimoto.A et al., "Synthesis of Asymmetrically Arranged Dendrimers With a Carbazole Dendron and a Phenylazomethine Dendron,", Macromolecules, 2004, vol. 37, pp. 5531-5537.

* cited by examiner solution

Thin Film

CARBAZOLE COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a carbazole compound. In addition, one embodiment of the present invention relates to a light-emitting element, a light-emitting device, an electronic device, and a lighting device each of which uses the carbazole compound.

2. Description of the Related Art

In recent years, research and development of light-emitting elements using electroluminescence (EL) have been actively conducted. In a basic structure of such a light-emitting element, a layer containing a light-emitting substance is interposed between a pair of electrodes. By voltage application to this element, light emission can be obtained from the light-emitting substance.

Such a light-emitting element is of self-luminous type, and thus has advantages over a liquid crystal display in that visibility of pixels is high, backlight is not needed, and so on. Therefore, such a light-emitting element is regarded as being suitable as a flat panel display element. Besides, such a light-emitting element has advantages in that it can be fabricated to be thin and lightweight, and has very fast response speed.

Furthermore, since such light-emitting elements can be formed in a film form, they make it possible to provide planar light emission easily; thus, large-area elements using planar light emission can be formed. This is a feature that is difficult to obtain for point light sources typified by an incandescent lamp and an LED or linear light sources typified by a fluorescent lamp. Therefore, the light-emitting element is very effective for use as a surface light source applicable to a lighting device and the like.

Light-emitting elements utilizing electroluminescence are broadly classified according to whether they use an organic compound or an inorganic compound as a light-emitting substance. In the case where an organic compound is used as a light-emitting substance, by application of voltage to a light-emitting element, electrons and holes are injected into a layer containing the light-emitting organic compound from a pair of electrodes, whereby current flows. Then, with these carriers (i.e., electrons and holes), the light-emitting organic compound is brought into an excited state. The light-emitting organic compound returns to the ground state from the excited state, thereby emitting light.

Because of such a mechanism, the light-emitting element is called a current-excitation light-emitting element. Note that the excited state of an organic compound can be a singlet excited state (S*) and a triplet excited state (T*), and luminescence from the singlet excited state is referred to as fluorescence, and luminescence from the triplet excited state is referred to as phosphorescence. The statistical generation ratio thereof in the light-emitting element is considered to be S*:T*=1:3. Accordingly, a light-emitting element including a phosphorescent compound is thought to be able to have emission efficiency three to four times that of a light-emitting element including a fluorescent compound. In recent years, a highly efficient light-emitting element including a phosphorescent compound has been actively developed.

In a light-emitting element including such a phosphorescent compound, a light-emitting layer is often formed such that the phosphorescent compound is dispersed in a matrix of another compound in order to suppress concentration quenching or quenching due to triplet-triplet annihilation in the phosphorescent compound. Here, the compound serving as the matrix is called host material, and the phosphorescent compound or the like dispersed in the matrix is called guest material.

Note that in the case where a phosphorescent compound is used as a guest material, a host material is needed to have larger triplet excitation energy (an energy difference between a ground state and a triplet excited state) than the phosphorescent compound. In addition, the use of an optimum host material for a guest material is needed in developing element characteristics of the light-emitting element. Therefore, in development of a highly efficient light-emitting element including a phosphorescent compound, development of a novel substance that can be used as a host material for the phosphorescent compound is also extremely regarded as important (e.g., Patent Document 1).

REFERENCE

Patent Document

[Patent Document 1] Japanese Published Patent Application No. 2009-227604

SUMMARY OF THE INVENTION

According to one embodiment of the present invention, a novel carbazole compound is provided which can be used as a host material for a light-emitting substance (substance emitting fluorescence or substance emitting phosphorescence). Further, according to one embodiment of the present invention, a novel carbazole compound which has both a hole-transport property and an electron-transport property, i.e., what is called a bipolar property, is provided. According to one embodiment of the present invention, a light-emitting element with high emission efficiency is provided. According to one embodiment of the present invention, a light-emitting device, an electronic device, or a lighting device with low power consumption is provided.

One embodiment of the present invention is a carbazole compound. Thus, one embodiment of the present invention is a carbazole compound represented by General Formula (G1) below.

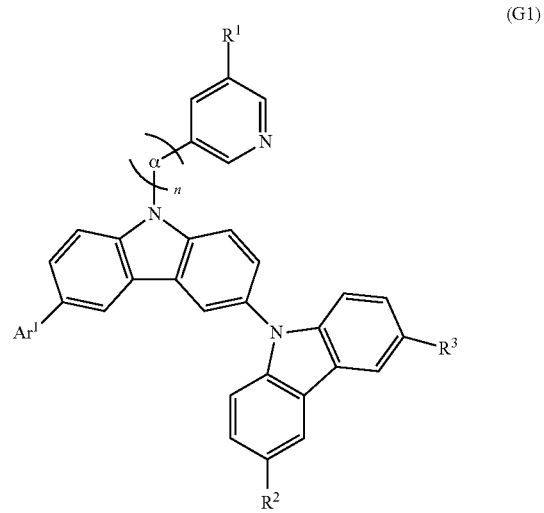

In the formula, $Ar^1$ represents any of hydrogen, a substituted or unsubstituted phenyl group, and a carbazolyl group represented by General Formula (G1-1) below; $R^1$ to $R^3$ each independently represent any of hydrogen, a substituted or unsubstituted phenyl group, and a substituted or unsubstituted biphenyl group; α represents any of a substituted or unsubstituted phenylene group and a substituted or unsubstituted biphenylene group; and n is any of 0, 1, and 2.

(G1-1)

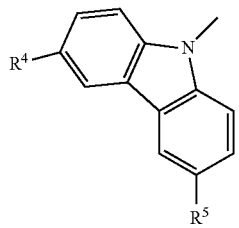

Note that in the formula, $R^4$ and $R^5$ each independently represent any of hydrogen, a substituted or unsubstituted phenyl group, and a substituted or unsubstituted biphenyl group.

Another embodiment of the present invention is a carbazole compound represented by General Formula (G2) below.

(G2)

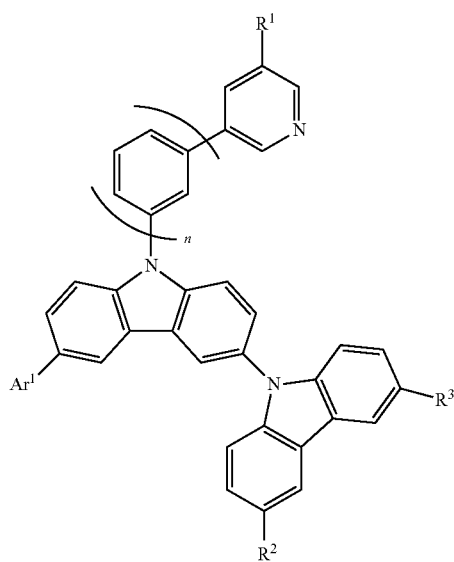

In the formula, $Ar^1$ represents any of hydrogen, a substituted or unsubstituted phenyl group, and a carbazolyl group represented by General Formula (G2-1) below; $R^1$ to $R^3$ each independently represent any of hydrogen, a substituted or unsubstituted phenyl group, and a substituted or unsubstituted biphenyl group; and n is any of 0, 1, and 2.

(G2-1)

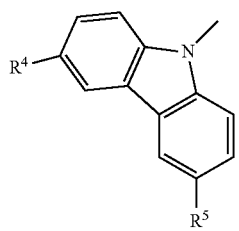

Note that in the formula, $R^4$ and $R^5$ each independently represent any of hydrogen, a substituted or unsubstituted phenyl group, and a substituted or unsubstituted biphenyl group.

A further embodiment of the present invention is a carbazole compound represented by General Formula (G3) below.

(G3)

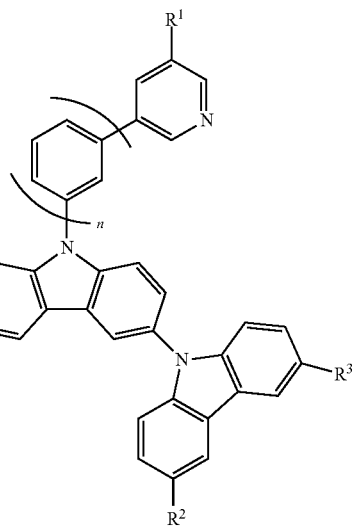

Note that in the formula, $R^1$ to $R^5$ each independently represent any of hydrogen, a substituted or unsubstituted phenyl group, and a substituted or unsubstituted biphenyl group. Further, n is any of 0, 1, and 2.

A still further embodiment of the present invention is a carbazole compound represented by General Formula (G4) below.

(G4)

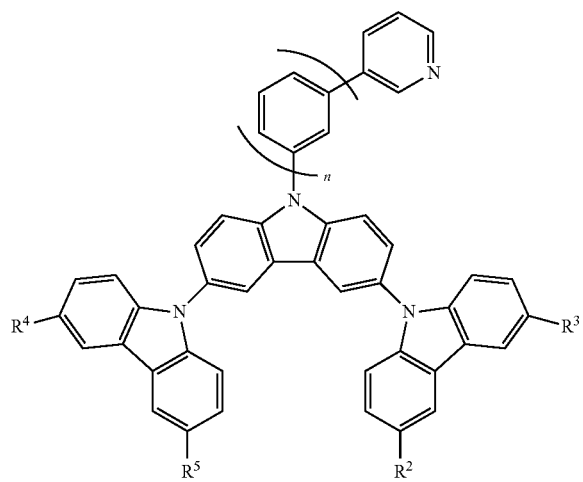

Note that in the formula, $R^2$ to $R^5$ each independently represent any of hydrogen, a substituted or unsubstituted phenyl group, and a substituted or unsubstituted biphenyl group. Further, n is any of 0, 1, and 2.

A yet still further embodiment of the present invention is a carbazole compound represented by Structural Formula (100) or (101) below.

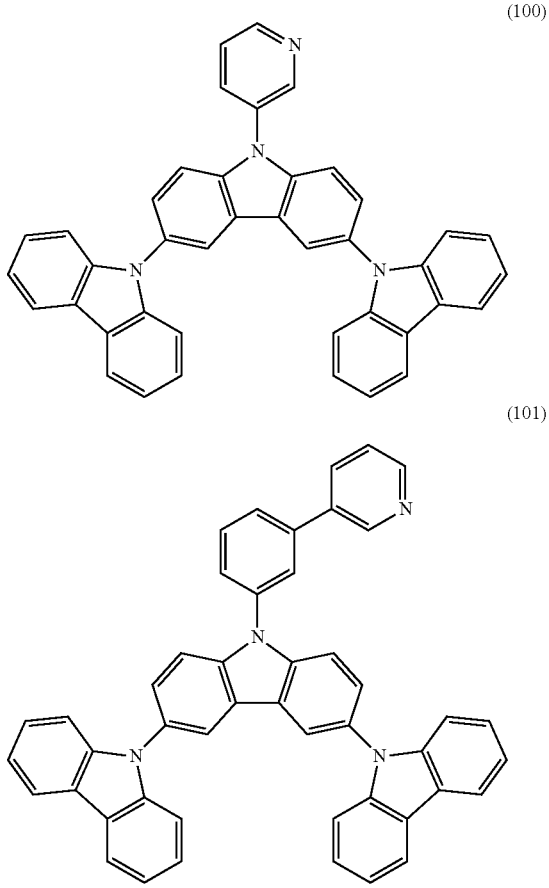

A carbazole compound of one embodiment of the present invention has both a hole-transport property and an electron-transport property, i.e., what is called a bipolar property. In addition, the carbazole compound features good thermo-physical properties and a high level of amorphousness. Therefore, the carbazole compound can be used for a hole-injection layer, a hole-transport layer, a light-emitting layer, or an electron-transport layer in a light-emitting element. In the carbazole compound of one embodiment of the present invention, the 9-position of carbazole is bonded to the 3-position (or the 3- and 6-positions) of carbazole, the 9-position of which is bonded to a pyridiyl group or an aryl group including pyridine. The structure in which the carbazole is bonded at the 9-position can suppress extension of conjugation to another substituent (the carbazole or the aryl group including the pyridine). Hence, the carbazole compound can also be used as a host material for a light-emitting material which emits relatively short-wavelength light, in a structure where the host material and the guest material (light-emitting material) constitute a light-emitting layer. Furthermore, the carbazole compound of one embodiment of the present invention is a fluorescent compound and therefore can also be used as a light-emitting substance of a light-emitting layer. Thus, the present invention also includes a light-emitting element using the carbazole compound of one embodiment of the present invention.

That is, a yet still further embodiment of the present invention is a light-emitting element which includes an EL layer between a pair of electrodes, where at least one of a light-emitting layer and a hole-transport layer which are included in the EL layer contains the carbazole compound of one embodiment of the present invention.

Further, the present invention includes, in its category, electronic devices and lighting devices including light-emitting devices as well as light-emitting devices including light-emitting elements. The light-emitting device in this specification refers to an image display device, a light-emitting device, and a light source (e.g., a lighting device). In addition, the light-emitting device includes, in its category, all of a module in which a light-emitting device is connected to a connector such as a flexible printed circuit (FPC), a tape automated bonding (TAB) tape or a tape carrier package (TCP), a module in which a printed wiring board is provided on the tip of a TAB tape or a TCP, and a module in which an integrated circuit (IC) is directly mounted on a light-emitting element by a chip on glass (COG) method.

Since the carbazole compound of one embodiment of the present invention has a high $S_1$ level, as a host material for a substance emitting fluorescence, the carbazole compound can be used in a light-emitting region of the visible region. In addition, since the carbazole compound of one embodiment of the present invention has a high $T_1$ level, as a host material for a substance emitting phosphorescence, the carbazole compound can be used in a light-emitting region of the visible region. Since the carbazole compound of one embodiment of the present invention has a bipolar property, it can be used for a hole-injection layer, a hole-transport layer, a light-emitting layer, or an electron-transport layer which is included in an EL layer of a light-emitting element. Note that a light-emitting element which is formed using the carbazole compound of one embodiment of the present invention for its hole-injection layer, its hole-transport layer, its light-emitting layer, its electron-transport layer, or the like can have high emission efficiency. By the use of such a light-emitting element, a light-emitting device, an electronic device, and a lighting device each having low power consumption and low drive voltage can be provided.

BRIEF DESCRIPTION OF THE DRAWINGS

In the accompanying drawings.

DETAILED DESCRIPTION OF THE INVENTION

Figure 1:
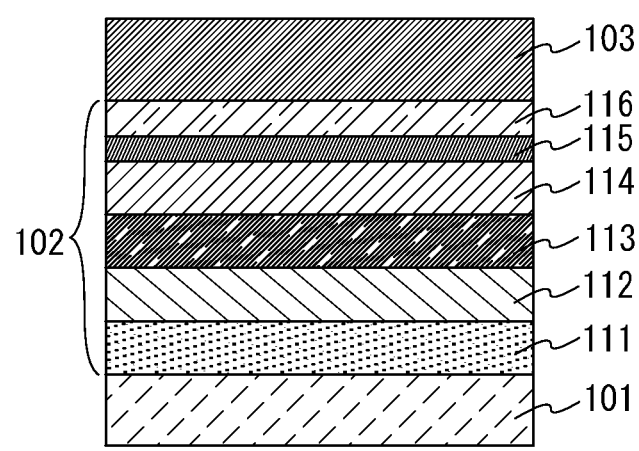
FIG. 1 illustrates a structure of a light-emitting element.

Hereinafter, embodiments of the present invention will be described in detail with reference to the accompanying drawings. Note that the present invention is not limited to the description below, and modes and details thereof can be modified in various ways without departing from the spirit and the scope of the present invention. Therefore, the present invention should not be construed as being limited to the description of the following embodiments.

Embodiment 1

In this embodiment, a carbazole compound of one embodiment of the present invention will be described.

A carbazole compound of one embodiment of the present invention is represented by General Formula (G1) below.

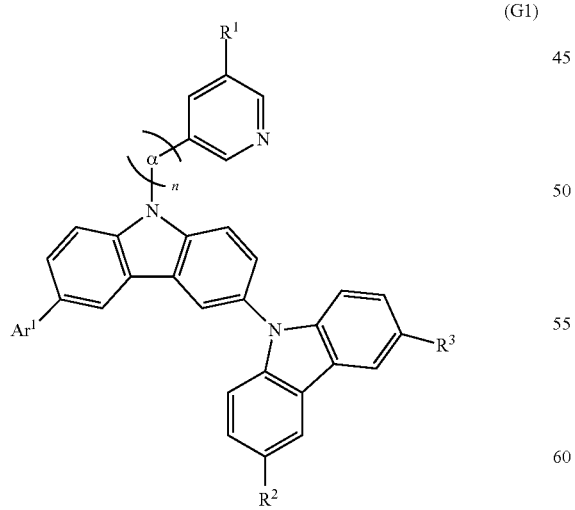

(G1)

In General Formula (G1), Ar$^1$ represents any of hydrogen, a substituted or unsubstituted phenyl group, and a carbazolyl group represented by General Formula (G1-1) below; R$^1$ to R$^3$ each independently represent any of hydrogen, a substituted or unsubstituted phenyl group, and a substituted or unsubstituted biphenyl group; α represents any of a substituted or unsubstituted phenylene group and a substituted or unsubstituted biphenylene group; and n is any of 0, 1, and 2.

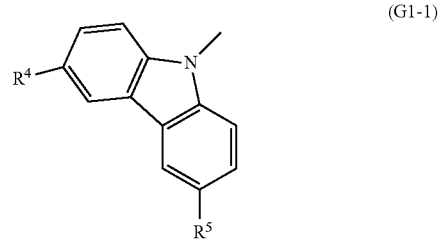

(G1-1)

In General Formula (G1-1), R$^4$ and R$^5$ each independently represent any of hydrogen, a substituted or unsubstituted phenyl group, and a substituted or unsubstituted biphenyl group.

Note that the site of substitution of the pyridine skeleton in General Formula (G1) above is the 3-position (or each of the 3- and 5-positions) of the pyridine skeleton. This structure is favorable because a carrier-transport (electron-transport) property is high and drive voltage is low as compared to the case where the site of substitution is the 2-position (or each of the 2- and 5-positions).

Note that Structural Formulae (s-1) to (s-8) below represent specific examples of the substituted or unsubstituted phenylene group or the substituted or unsubstituted biphenylene group which is represented by α in General Formula (G1). One or more alkyl groups each having 1 to 6 carbon atoms may be bonded to α as a substituent. It is preferable that α have a substituent because in that case the structure becomes sterical and film quality is expected to improve. This structure is preferable also because solubility in an organic solvent is increased to allow facilitated synthesis and favorable film formation by a wet method. A structure where α is unsubstituted is also favorable because in that case a carrier-transport property is expected to improve.

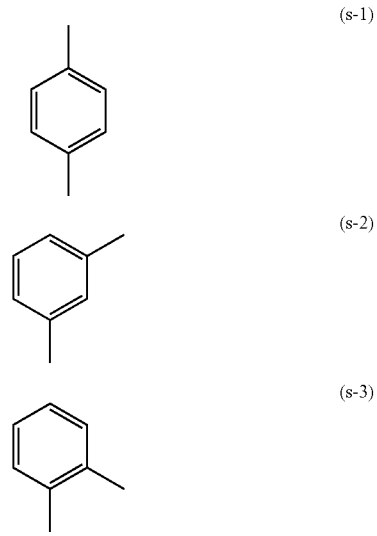

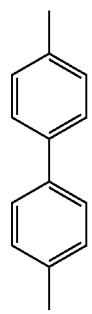
(s-4)

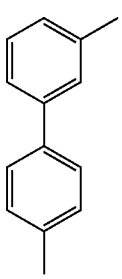
(s-5)

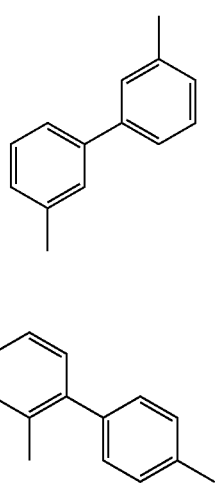
(s-6)

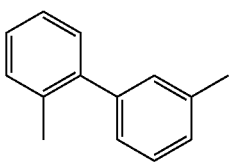
(s-7)

(s-8)

The bond at the meta-position or the ortho-position as in Structural Formulae (s-2), (s-3), and (s-5) to (s-8) is preferred in that conjugation is unlikely to extend. In addition, the structure becomes sterical, which is also preferable. The bond at the para-position as in Structural Formulae (s-1) and (s-4) is preferred in that improved a carrier-transport property and increased reliability can be expected.

A carbazole compound of one embodiment of the present invention is represented by General Formula (G2) below.

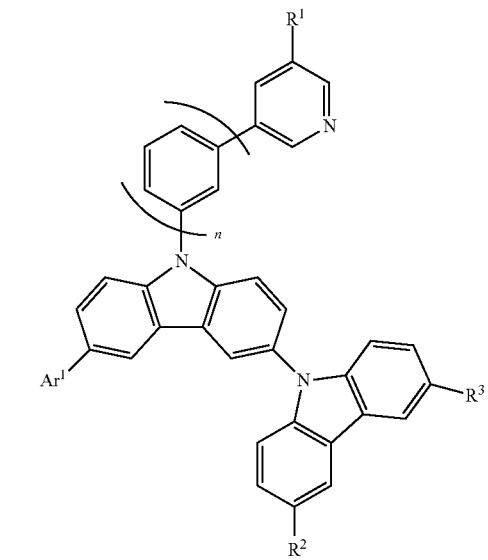
(G2)

In General Formula (G2), $Ar^1$ represents any of hydrogen, a substituted or unsubstituted phenyl group, and a carbazolyl group represented by General Formula (G2-1) below; $R^1$ to $R^3$ each independently represent any of hydrogen, a substituted or unsubstituted phenyl group, and a substituted or unsubstituted biphenyl group; and n is any of 0, 1, and 2.

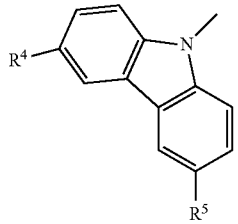
(G2-1)

Note that in General Formula (G2-1), $R^4$ and $R^5$ each independently represent any of hydrogen, a substituted or unsubstituted phenyl group, and a substituted or unsubstituted biphenyl group.

Note that $Ar^1$ in General Formula (G2) is preferably hydrogen, in which case a band gap (Bg) between the HOMO level and the LUMO level is widened and the carbazole compound can be favorably used as a host material for a light-emitting material which emits light with a shorter wavelength. Alternatively, $Ar^1$ in General Formula (G2) preferably has a carbazole skeleton represented by General Formula (G2-1), in which case a carrier-transport property is increased. In addition, $R^2$ and $R^4$ are preferably the same substituents and $R^3$ and $R^5$ are preferably the same substituents, in which case the synthesis is facilitated (in addition, $R^2$ to $R^5$ are preferably hydrogen to further facilitate the synthesis).

A carbazole compound of one embodiment of the present invention is represented by General Formula (G3) below.

(G3)

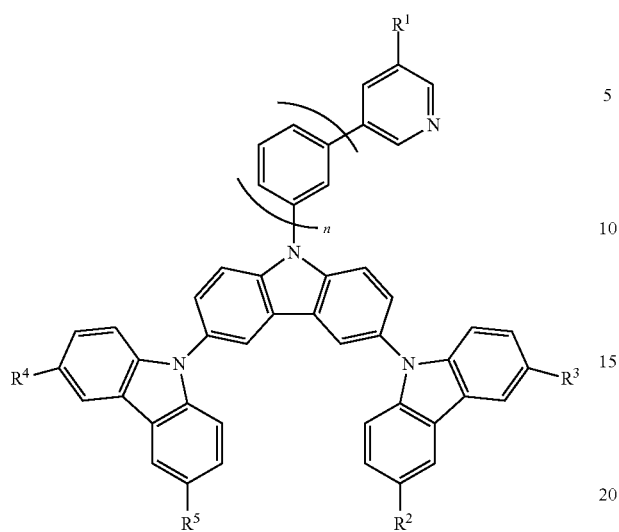

In General Formula (G3), $R^1$ to $R^5$ each independently represent any of hydrogen, a substituted or unsubstituted phenyl group, and a substituted or unsubstituted biphenyl group. Further, n is any of 0, 1, and 2.

Note that $R^1$ in General Formula (G3) is preferably hydrogen, in which case the $T_1$ level becomes higher and the carbazole compound can be favorably used as a host material for a phosphorescent material emitting short-wavelength light. Similarly, $R^2$ to $R^5$ are also preferably hydrogen, in which case the $T_1$ level becomes higher and the carbazole compound can be favorably used as a host material for a phosphorescent material emitting short-wavelength light. Alternatively, $R^2$ to $R^5$ in General Formula (G3) are preferably aryl groups such as a phenyl group or a biphenyl group, in which case a carrier-transport property (especially hole-transport property) is further increased. At this time, the biphenyl group is preferably a metabiphenyl group or an orthobiphenyl group, in which case the $T_1$ level becomes higher and the band gap (Bg) is widened.

In addition, n in General Formula (G3) is preferably 1 or more, in which case conjugation between pyridine that is an electron-transport skeleton and carbazole that is a hole-transport skeleton is not readily extended, leading a higher $T_1$ level.

A carbazole compound of one embodiment of the present invention is represented by General Formula (G4) below.

(G4)

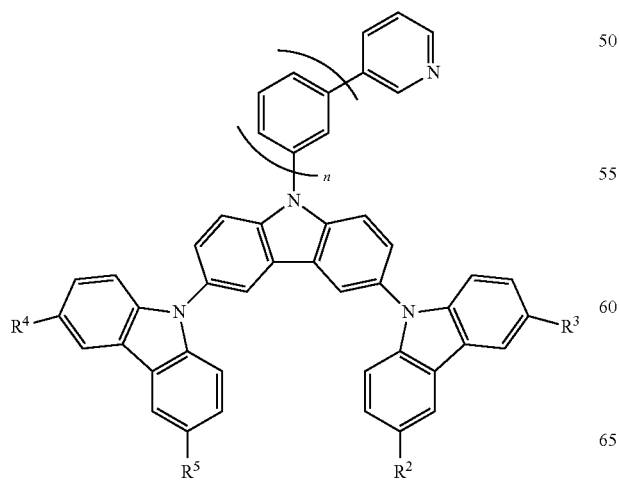

In General Formula (G4), $R^2$ to $R^5$ each independently represent any of hydrogen, a substituted or unsubstituted phenyl group, and a substituted or unsubstituted biphenyl group. Further, n is any of 0, 1, and 2.

Next, specific structural formulae of the carbazole compound of one embodiment of the present invention are shown (Structural Formulae (100) to (111) below). Note that the present invention is not limited thereto.

(100)

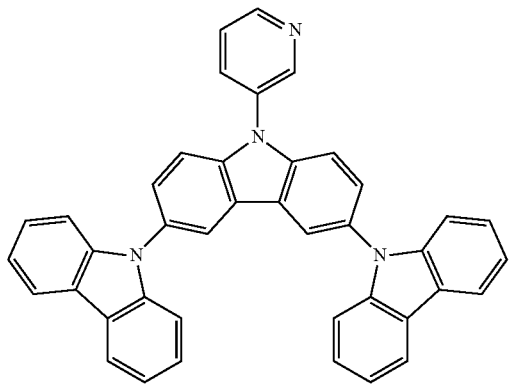

(101)

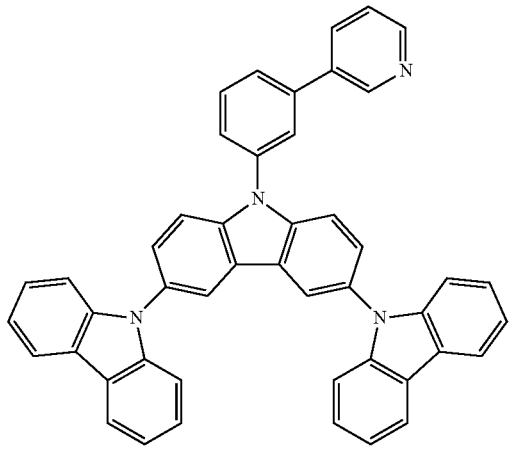

(102)

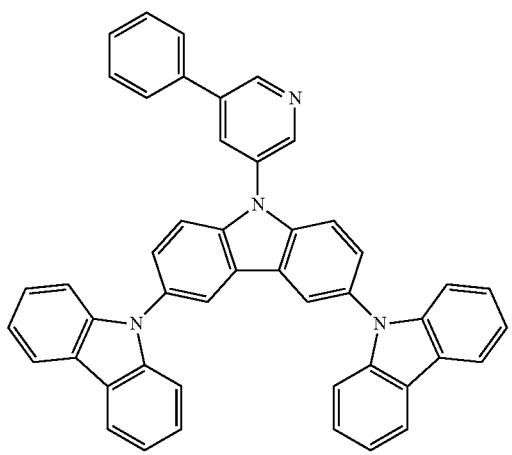

(103)
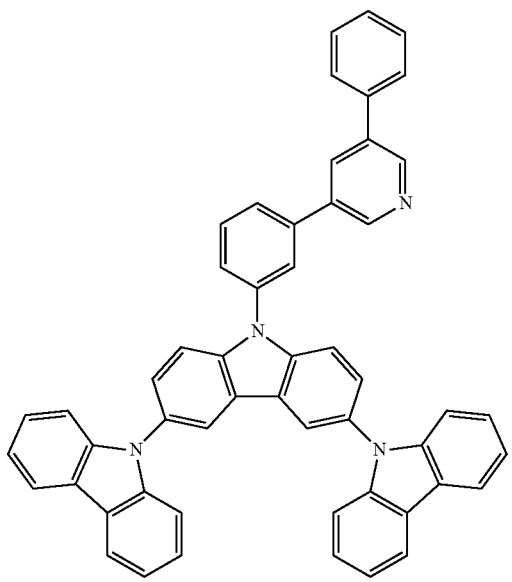
(104)
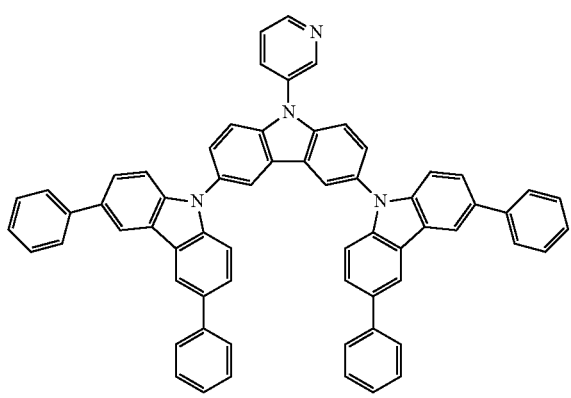
(105)
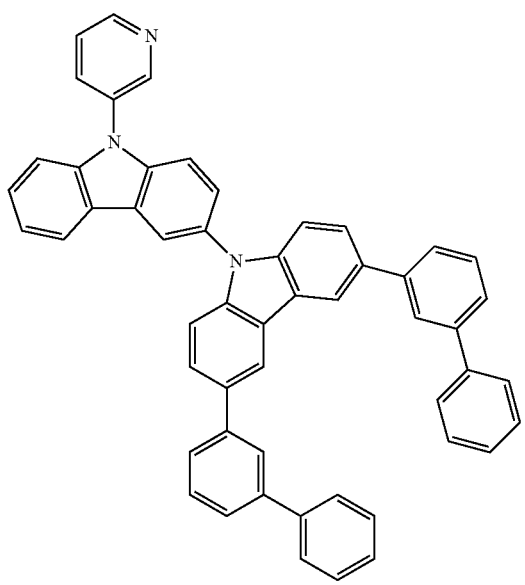
(106)
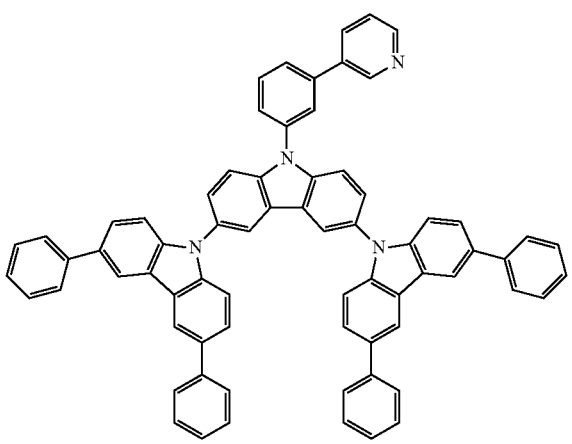
(107)
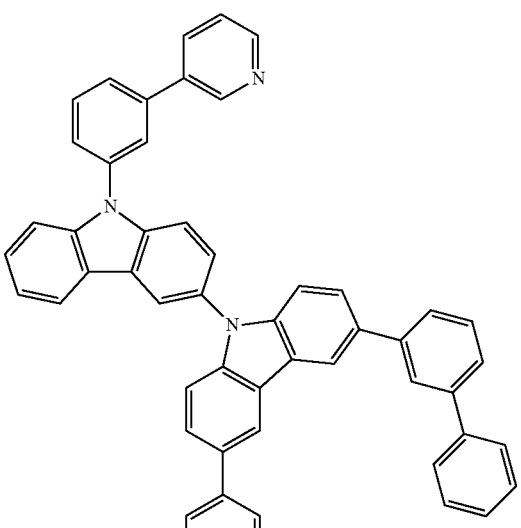
(108)
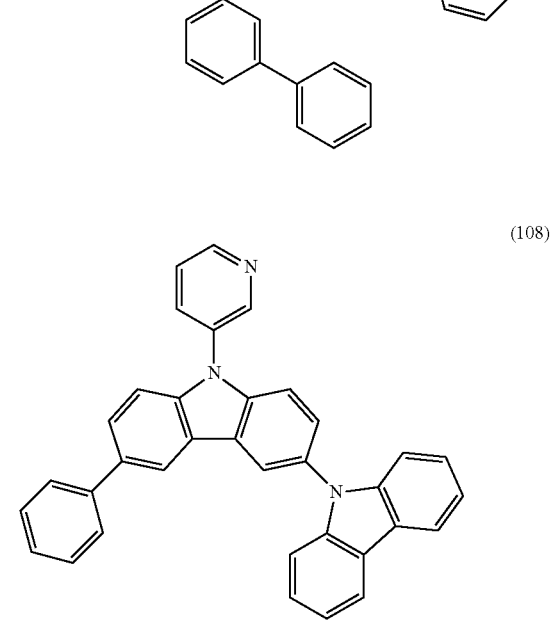

(109)

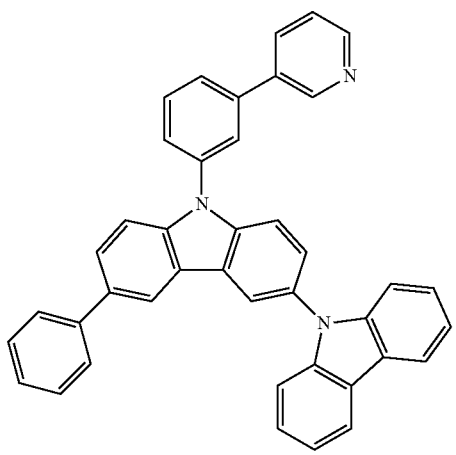

(110)

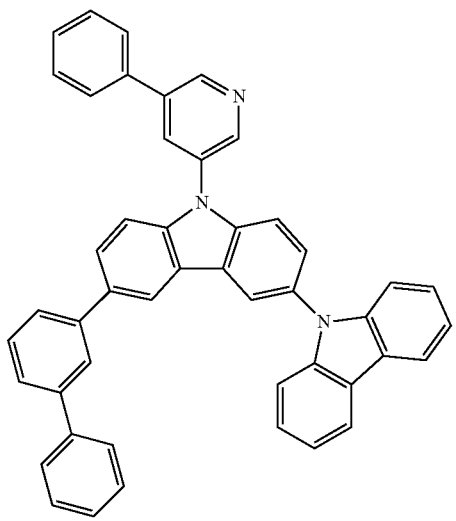

(111)

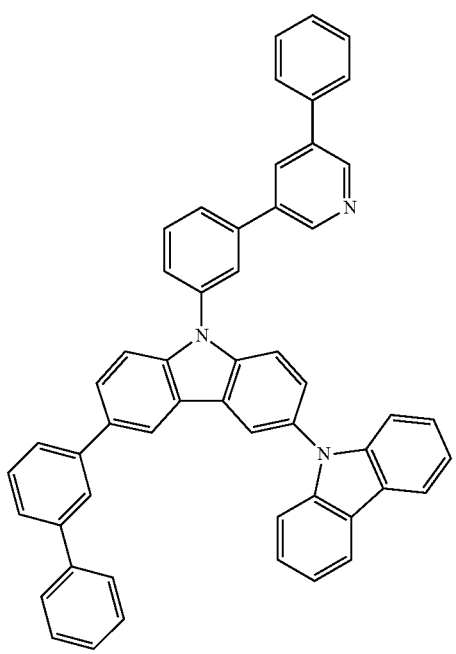

Note that carbazole compounds represented by Structural Formulae (100) to (111) above are novel substances which have high bipolar properties. Specifically, their pyridine skeletons excel in an electron-transport property and their carbazole skeletons excel in a hole-transport property.

Next, as an example of a method of synthesizing the carbazole compound of one embodiment of the present invention, a method of synthesizing the carbazole compound represented by General Formula (G1) is described.

<<Method of Synthesizing Carbazole Compound Represented by General Formula (G1)>>

An example of a method of synthesizing the carbazole compound represented by General Formula (G1) below is described.

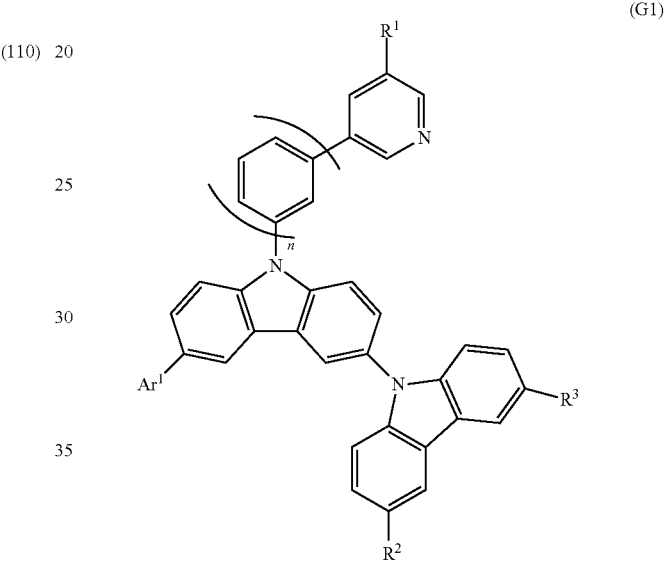

(G1)

A method of synthesizing the carbazole compound represented by General Formula (G1) is shown in Synthesis Scheme (A) below.

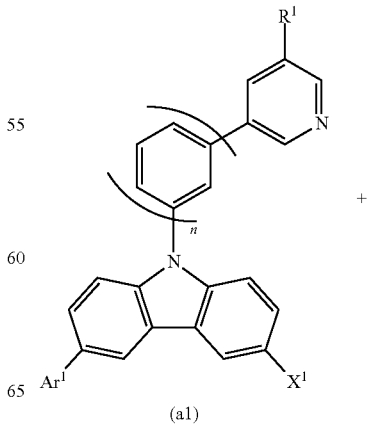

(a1)

(A)

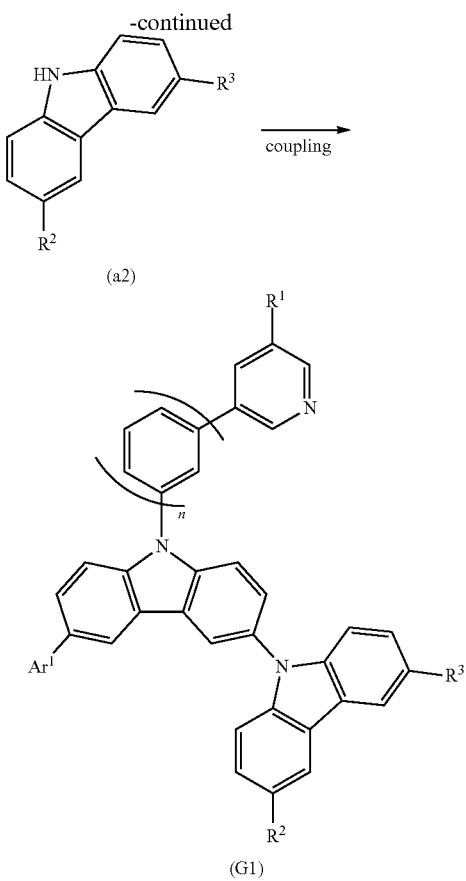

Note that Ar$^1$ and R$^1$ to R$^3$ in the formula are substituents similar to Ar$^1$ and R$^1$ to R$^3$ in General Formula (G1) which has already been described. Similarly, n is any of 0, 1, and 2. Further, X$^1$ represents a halogen group; iodine, bromine, and chlorine are preferred in descending order according to reactivity.

In the synthesis method shown in Synthesis Scheme (A) above, the carbazole compound represented by General Formula (G1) above is obtained by coupling a halogenated carbazole compound (a1) and a carbazole compound (a2).

There are a variety of reaction conditions for the coupling reaction between the aryl compound including the halogen group and the 9-position of the carbazole, which is shown in Synthesis Scheme (A); for example, the Buchwald-Hartwig reaction which uses a metal catalyst in the presence of a base can be employed.

In the Buchwald-Hartwig reaction, a palladium catalyst can be used as a metal catalyst, and a mixture of a palladium complex and a ligand thereof can be used as the palladium catalyst. Examples of the palladium complex include bis(dibenzylideneacetone)palladium(0) and palladium(II) acetate. Examples of the ligand include tri(tert-butyl)phosphine, tri(n-hexyl)phosphine, tricyclohexylphosphine, and 1,1-bis(diphenylphosphino)ferrocene (abbreviation: DPPF). Examples of a substance which can be used as a base are organic bases such as sodium tert-butoxide, inorganic bases such as potassium carbonate, and the like. The reaction is preferably performed in a solution, and toluene, xylene, benzene, and the like are given as a solvent that can be used in the reaction. However, the catalyst, ligand, base, and solvent which can be used are not limited to these examples. In addition, the reaction is preferably performed under an inert atmosphere of nitrogen, argon, or the like.

As a coupling method in Synthesis Scheme (A) above, the Ullmann reaction can also be employed. In that case, a copper catalyst is used as a metal catalyst (e.g., copper(I) iodide or copper(II) acetate). Examples of a substance that can be used as a base include an inorganic base such as potassium carbonate. The reaction is preferably performed in a solution, and 1,3-dimethyl-3,4,5,6-tetrahydro-2(1H)-pyrimidinone (abbreviation: DMPU), toluene, xylene, benzene, and the like can be given as a solvent that can be used. However, the catalyst, base, and solvent which can be used are not limited to these examples. In addition, the reaction is preferably performed under an inert atmosphere of nitrogen, argon, or the like.

Note that a solvent having a high boiling point such as DMPU or xylene is preferably used because, in the Ullmann reaction, an object can be obtained in a shorter time and at a higher yield when the reaction temperature is equal to or more than 100° C. In particular, DMPU is more preferable because the reaction temperature is more preferably 150° C. or higher.

Note that as a method of synthesizing the carbazole compound of one embodiment of the present invention, Synthesis Scheme (A) above, which has already been described as an example of the synthesis method, can be easily and favorably used. Moreover, in synthesis of the halogenated carbazole compound (a1) in Synthesis Scheme (A) above, the carbazole skeleton having hydrogen at the 3-position (or the 3- and 6-positions) is reacted with the use of a halogenating agent, whereby the 3-position (or the 3- and 6-positions) can be specifically-halogenated and the synthetic yield can be high (here, even when an aryl group is bonded to the 9-position as in the halogenated carbazole compound (a1), this aryl group is not readily halogenated). In addition, since an aryl group is already bonded to the halogenated carbazole compound (a1) at the 9-position, at the time of coupling with the carbazole compound (a2), the reaction can proceed with high purity and yield, which is preferable (a side reaction is not caused in which the 9-position of the halogenated carbazole compound (a1) is bonded to the 3-position (or the 3- and 6-positions) of the halogenated carbazole compound (a1)). Note that N-bromosuccinimide (abbreviation: NBS), bromine, or iodine can be given as the halogenating agent.

There are other methods of synthesizing the carbazole compound of one embodiment of the present invention, one of which is as follows: not an aryl group including pyridine but a protecting group is bonded to the 9-position of the halogenated carbazole compound (a1) and the carbazole compound (a2) is then coupled to the 3-position (or the 3- and 6-positions) of the halogenated carbazole compound (a1); after that, the protecting group at the 9-position is removed and the aryl group including pyridine is coupled to the 9-position. In other words, the present invention is not limited to the above-described synthesis method and any other synthesis method may be employed.

Since the above-described carbazole compound of one embodiment of the present invention has a high S$_1$ level, as a host material for a substance emitting fluorescence, the carbazole compound can be used in a light-emitting region of the visible region. In addition, since the carbazole compound of one embodiment of the present invention has a high T$_1$ level, as a host material for a substance emitting phosphorescence, the carbazole compound can be used in a light-emitting region of the visible region. Since the carbazole compound of one embodiment of the present invention has a high bipolar property, it can be used as a carrier-transport material in a light-emitting element.

The use of the carbazole compound of one embodiment of the present invention allows a light-emitting element to have high emission efficiency, and a drive voltage increase of the light-emitting element to be minimized. Further, by the use of such a light-emitting element, a light-emitting device, an electronic device, or a lighting device having low power consumption can be obtained.

The structure described in this embodiment can be combined as appropriate with any of the structures described in the other embodiments.

Embodiment 2

In this embodiment, as one embodiment of the present invention, a light-emitting element in which the carbazole compound described in Embodiment 1 can be used will be described with reference to FIG. 1.

In a light-emitting element described in this embodiment, as illustrated in FIG. 1, an EL layer 102 including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge generation layer (E) 116, and the like in addition to the light-emitting layer 113.

By application of a voltage to such a light-emitting element, holes injected from the first electrode 101 side and electrons injected from the second electrode 103 side recombine in the light-emitting layer 113 to raise a substance contained in the light-emitting layer 113 to an excited state. Then, light is emitted when the substance in the excited state returns to the ground state.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge generation layer (E) 116 is a layer containing a substance having a high hole-transport property and an acceptor substance. Electrons are extracted from the substance having a high hole-transport property owing to the acceptor substance, and the extracted electrons are injected from the electron-injection layer 115 having an electron-injection property into the light-emitting layer 113 through the electron-transport layer 114.

Specific examples regarding manufacture of the light-emitting element described in this embodiment are described below.

As the first electrode (anode) 101 and the second electrode (cathode) 103, a metal, an alloy, an electrically conductive compound, a mixture thereof, and the like can be used. Specifically, indium oxide-tin oxide (ITO: indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (e.g., MgAg and AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

As the substance with a high hole-transport property used for the hole-injection layer 111, the hole-transport layer 112, and the charge generation layer (E) 116, the following can be given, for example: aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). In addition, the following carbazole compounds and the like can be used: 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA). The substances mentioned here are mainly ones that have a hole mobility of $10^{-6}$ cm$^2$/Vs or higher. However, other than the above-described substances, any substance that has a property of transporting more holes than electrons may be used.

Further, a polymer such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

Note that as the substance having a high hole-transport property, it is also possible to use the carbazole compound of one embodiment of the present invention.

As examples of the acceptor substance that is used for the hole-injection layer 111 and the charge generation layer (E) 116, a transition metal oxide or an oxide of a metal belonging to any of Group 4 to Group 8 of the periodic table can be given. Specifically, molybdenum oxide is particularly preferable.

In particular, the carbazole compound of one embodiment of the present invention, which has a bipolar property, can be suitably used for the hole-injection layer 111 and the charge generation layer (E) 116 as a mixture with the above acceptor substance. Alternatively, a bipolar organic compound in which an electron-transport skeleton and a hole-transport skeleton are combined can also be used as a mixture with such an acceptor substance.

The light-emitting layer 113 is a layer containing a light-emitting substance. The light-emitting layer 113 may contain only a light-emitting substance; alternatively, an emission center substance may be dispersed in a host material in the light-emitting layer 113.

There is no particular limitation on materials that can be used as the light-emitting substance and the emission center substance in the light-emitting layer 113, and light emitted from these substances may be either fluorescence or phosphorescence. Described below are examples of the light-emitting substance and the emission center substance.

Examples of a substance which emits fluorescence include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N'N'-tetrakis(4-methylphenyl)acenaphtho[1,2-α]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM).

Note that as the substance which emits fluorescence, it is also possible to use the carbazole compound of one embodiment of the present invention.

Examples of a substance which emits phosphorescence include bis[2-(3',5'-bistrifluoromethylphenyl)pyridinato-N,$C^{2'}$]iridium(III)picolinate (abbreviation: Ir($CF_3$ppy)$_2$(pic)), bis[2-(4',6'-difluorophenyl)pyridinato-N,$C^{2'}$]iridium(III)acetylacetonate (abbreviation: FIracac), tris(2-phenylpyridinato)iridium(III) (abbreviation: Ir(ppy)$_3$), bis(2-phenylpyridinato)iridium(III)acetylacetonate (abbreviation: Ir(ppy)$_2$(acac)), tris(acetylacetonato)(monophenanthroline)terbium (III) (abbreviation: Tb(acac)$_3$(Phen)), bis(benzo[h]quinolinato)iridium(III)acetylacetonate (abbreviation: Ir(bzq)$_2$(acac)), bis(2,4-diphenyl-1,3-oxazolato-N,$C^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), bis[2-(2'-benzo[4,5-α]thienyl)pyridinato-N,$C^{3'}$]iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

The HOMO level and the LUMO level of an iridium complex including a pyridine skeleton (where iridium is preferably bonded to the pyridine skeleton to form an ortho-metalated structure) tend to be close to the HOMO level and the LUMO level of the carbazole compound of one embodiment of the present invention. The reason for this is that the carbazole compound also includes a pyridine skeleton. Thus, such a complex can favorably give and receive carriers to and from a host material. Such a complex is preferably used, in which case an element that can be driven at low voltage and has high efficiency can be easily obtained. Specific examples include tris(2-phenylpyridinato)iridium(III) (abbreviation: Ir(ppy)$_3$), bis(2-phenylpyridinato)iridium(III)acetylacetonate (abbreviation: Ir(ppy)$_2$(acac)), and bis[2-(2'-benzo[4,5-α]thienyl)pyridinato-N,$C^{3'}$]iridium(III)acetylacetonate (abbreviation: Ir(btp)$_2$(acac)).

There is no particular limitation on a material that can be used as the above host material, and for example, a metal complex, a heterocyclic compound, or an aromatic amine compound can be used. Examples of the metal complex include tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), bis[2-(2-benzothiazolyl)phenolato]zinc(II) (abbreviation: ZnBTZ), and the like. Examples of the heterocyclic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: Bphen), bathocuproine (abbreviation: BCP), 9-[4-(5-phenyl-1,3,4-oxadiazol-2-yl)phenyl]-9H-carbazole (abbreviation: CO11), and the like. Examples of the aromatic amine compound include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), and the like. In addition, condensed polycyclic aromatic compounds such as anthracene derivatives, phenanthrene derivatives, pyrene derivatives, chrysene derivatives, and dibenzo[g,p]chrysene derivatives are given. Specific examples include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)

triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N'',N'',N''',N'''-octaphenyldibenzo[g,p]chrysene-2,7,10,15-tetraamine (abbreviation: DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), and the like. One or more substances having a wider energy gap than the above-described emission center substance can be selected from these substances and known substances. Moreover, in the case where the emission center substance emits phosphorescence, a substance having higher triplet excitation energy (an energy difference between a ground state and a triplet excited state) than the emission center substance can be selected as the host material.

Note that as the material that can be used as the above host material, it is also possible to use the carbazole compound of one embodiment of the present invention. Since the carbazole compound of one embodiment of the present invention has a high $S_1$ level, as a host material for a substance emitting fluorescence, the carbazole compound can be used in a light-emitting region of the visible region. In addition, since the carbazole compound of one embodiment of the present invention has a high $T_1$ level, as a host material for a substance emitting phosphorescence, the carbazole compound can be used in a light-emitting region of the visible region (light having a longer wavelength than blue light). The carbazole compound of one embodiment of the present invention can be favorably used especially because a host material for a material (specifically a phosphorescent material) that emits short-wavelength light such as blue light is still under development.

Note that the light-emitting layer 113 may have a structure in which two or more layers are stacked. For example, in the case where the light-emitting layer 113 is formed by stacking a first light-emitting layer and a second light-emitting layer in that order from the hole-transport layer side, for example, the first light-emitting layer is formed using a substance having a hole-transport property as the host material and the second light-emitting layer is formed using a substance having an electron-transport property as the host material.

The electron-transport layer 114 is a layer containing a substance having a high electron-transport property. For the electron-transport layer 114, metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$) can be used. Alternatively, a hetero aromatic compound such as 2-(4-biphenylyl)-5-(4-tert-butylphenyl)-1,3,4-oxadiazole (abbreviation: PBD), 1,3-bis[5-(4-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can be used. Further alternatively, a polymer such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances described here are mainly ones having an electron mobility of $10^{-6}$ $cm^2/Vs$ or higher. Note that other than these substances, any substance that has a property of transporting more electrons than holes may be used for the electron-transport layer.

Further, the electron-transport layer is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, or a compound thereof, such as lithium fluoride (LiF), cesium fluoride (CsF), calcium fluoride ($CaF_2$), or lithium oxide (LiOx), can be used. Alternatively, a rare earth metal compound such as erbium fluoride ($ErF_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, for example, the substances for forming the electron-transport layer 114 (e.g., a metal complex and a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like can be given. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, electron-injection layer 115, and charge generation layer (E) 116 can be formed by a method such as an evaporation method (e.g., a vacuum evaporation method), an ink-jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element is formed using the carbazole compound of one embodiment of the present invention, whereby the element efficiency of the light-emitting element can be improved and a drive voltage increase can be minimized.

Moreover, although it is preferable that the carbazole compound of one embodiment of the present invention be used as a host material for a phosphorescent substance in a light-emitting layer, the carbazole compound can also be used as a light-emitting substance in the light-emitting layer or a host material for a fluorescent substance in the light-emitting layer, or for another layer (e.g., hole-injection layer, hole-transport layer, or electron-transport layer); thus, it is possible that a plurality of layers include the same material. Accordingly, costs of synthesis of a material or manufacture of a light-emitting element can be reduced, and therefore the use of the carbazole compound is preferred.

Note that the light-emitting element described in this embodiment is an example of a light-emitting element manufactured using the carbazole compound of one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention. Note that the power consumption of these light-emitting devices can be reduced.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

Embodiment 3

In this embodiment, as one embodiment of the present invention, a light-emitting element in which two or more kinds of organic compounds as well as a phosphorescent compound are used for a light-emitting layer is described.

Figure 2:
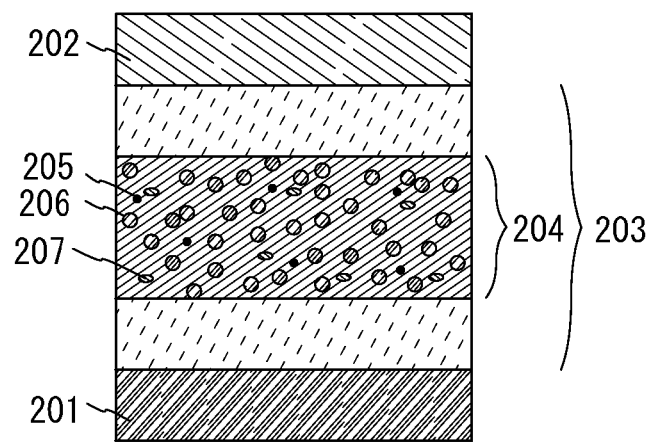
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may further include a hole-injection layer, a hole-transport layer, an electron-transport layer, an electron-injection layer, a charge generation layer (E), and the like. Note that for the hole-injection layer, the hole-transport layer, the electron-transport layer, the electron-injection layer, and the charge generation layer (E), the substances described in Embodiment 2 can be used.

The light-emitting layer 204 described in this embodiment contains a phosphorescent compound 205, a first organic compound 206, and a second organic compound 207. The carbazole compound described in Embodiment 1 can be used as the first organic compound 206 or the second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. This is because, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency decreases.

Here, for improvement in efficiency of energy transfer from the host material to the guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, because a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound and the second organic compound preferably forms an exciplex (also referred to as excited complex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound and the second organic compound are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is assumed to occur.

For the phosphorescent compound 205, a phosphorescent organometallic complex is preferably used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

Examples of a phosphorescent organometallic complex include bis[2-(3',5'-bistrifluoromethylphenyl)pyridinato-N, $C^{2'}$]iridium(III)picolinate (abbreviation: Ir(CF$_3$ ppy)$_2$(pic)), bis[2-(4',6'-difluorophenyl)pyridinato-N,$C^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III)acetylacetonate (abbreviation: Ir(ppy)$_2$(acac)), tris(acetylacetonato)(monophenanthroline)terbium(III) (abbreviation: Tb(acac)$_3$(Phen)), bis(benzo[h]quinolinato)iridium(III)acetylacetonate (abbreviation: Ir(bzq)$_2$(acac)), bis(2,4-diphenyl-1,3-oxazolato-N,$C^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,$C^{2'}$)iridium(III)acetylacetonate (abbreviation: Ir(bt)$_2$(acac)), bis[2-(2'-benzo[4,5-α]thienyppyridinato-N,$C^{3'}$]iridium(III)acetylacetonate (abbreviation: Ir(btp)$_2$(acac)), bis(1-phenylisoquinolinato-N,$C^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)).

As a compound which is likely to accept electrons, a π-electron deficient heteroaromatic compound such as a nitrogen-containing heteroaromatic compound is preferable. For example, a quinoxaline derivative or a dibenzoquinoxaline derivative can be given and examples thereof include: 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDB q-II), and 6-[3-(dibenzothiophen-4-yl)phenyl]dibenzo[f,h]quinoxaline (abbreviation: 6mDBTPDBq-II). Note that the carbazole compound of one embodiment of the present invention can be used as a compound which is likely to accept electrons since the carbazole compound has a bipolar property.

As a compound which is likely to accept holes, a π-electron rich heteroaromatic compound (e.g., a carbazole derivative or an indole derivative) or an aromatic amine compound is preferable. For example, the following can be given: 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2). Note that the carbazole compound of one embodiment of the present invention can be used as a compound which is likely to accept holes since the carbazole compound has a bipolar property.

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of the light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

Note that the light-emitting element described in this embodiment is an example of a structure of a light-emitting element; it is possible to apply a light-emitting element having another structure, which is described in another embodiment, to a light-emitting device of one embodiment of the present invention. Further, as a light-emitting device including the above light-emitting element, a passive matrix light-emitting device and an active matrix light-emitting device can be manufactured. It is also possible to manufacture a light-emitting device with a microcavity structure including the above light-emitting element, whose structure is changed as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an n-type TFT and a p-type TFT or only either an n-type TFT or a p-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

Embodiment 4

In this embodiment, as one embodiment of the present invention, a light-emitting element (hereinafter referred to as tandem light-emitting element) in which a charge generation layer is interposed between a plurality of EL layers will be described.

Figure 3A:
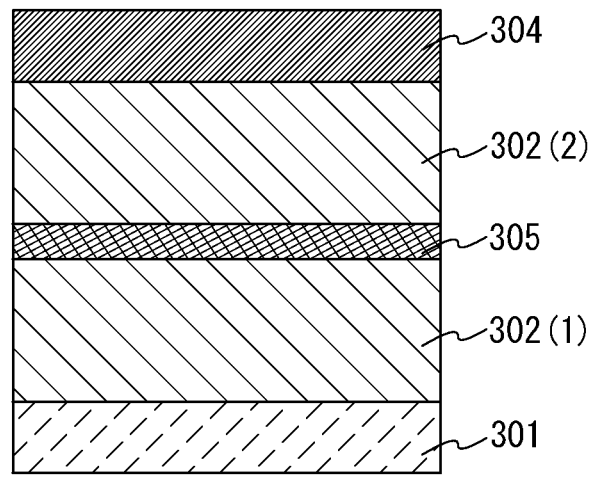
FIGS. 3A and 3B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 2. In addition, although the plurality of EL layers (the first EL layer 302(1) and the second EL layer 302(2)) may have structures similar to those described in Embodiment 2 or 3, any of the EL layers may have a structure similar to that described in Embodiment 2 or 3. In other words, the structures of the first EL layer 302(1) and the second EL layer 302(2) may be the same or different from each other and can be similar to those of the EL layers described in Embodiment 2 or Embodiment 3.

Further, a charge generation layer (I) 305 is provided between the plurality of EL layers (the first EL layer 302(1) and the second EL layer 302(2)). The charge generation layer (I) 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge generation layer (I) 305 injects electrons into the first EL layer 302(1) and injects holes into the second EL layer 302(2).

Note that in terms of light extraction efficiency, the charge generation layer (I) 305 preferably has a light-transmitting property with respect to visible light (specifically, the charge generation layer (I) 305 has a visible light transmittance of 40% or more). Further, the charge generation layer (I) 305 functions even if it has lower conductivity than the first electrode 301 or the second electrode 304.

The charge generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. However, other than the above-described substances, any organic compound that has a property of transporting more holes than electrons may be used. Note that it is also possible to use the carbazole compound of one embodiment of the present invention as the organic compound having a high hole-transport property in the charge generation layer (I) 305.

Further, as the electron acceptor, 7,7,8,8-tetracyano-2,3,5,6-tetrafluoroquinodimethane (abbreviation: F$_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these metal oxides, molybdenum oxide is especially preferable because it is stable in the air, has a low hygroscopic property, and is easily handled.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, Bphen, BCP, or the like. The substances mentioned here are mainly ones that have an electron mobility of $10^{-6}$ cm$^2$/Vs or higher. Note that other than the above-described substances, any organic compound that has a property of transporting more electrons than holes may be used.

As the electron donor, it is possible to use an alkali metal, an alkaline earth metal, a rare earth metal, a metal belonging to Group 2 or 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge generation layer (I) 305 by using any of the above materials can suppress a drive voltage increase caused by the stack of the EL layers.

Figure 3B:
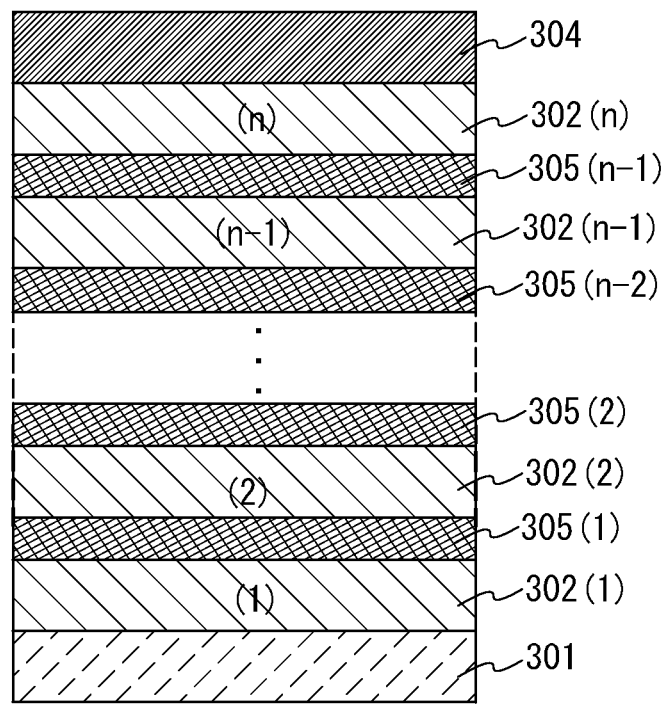

Although this embodiment shows the light-emitting element having two EL layers, the present invention can be similarly applied to a light-emitting element in which n EL layers (302(1) to 302(n)) (n is three or more) are stacked and charge generation layers (I) (305(1) to 305(n−1)) are each provided between these EL layers (302(1) to 302(n)) as illustrated in FIG. 3B. In the case where a plurality of EL layers are included between a pair of electrodes as in the light-emitting element according to this embodiment, by provision of a charge generation layer (I) between the EL layers, light emission in a high luminance region can be obtained with current density kept low. Since the current density can be kept low, the element can have a long lifetime. When the light-emitting element is applied to lighting, voltage drop due to resistance of an electrode material can be reduced, thereby achieving homogeneous light emission in a large area. Moreover, it is possible to achieve a light-emitting device of low power consumption, which can be driven at a low voltage.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when lights obtained from substances which emit light of complementary colors are mixed, white emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

Embodiment 5

Figure 4:
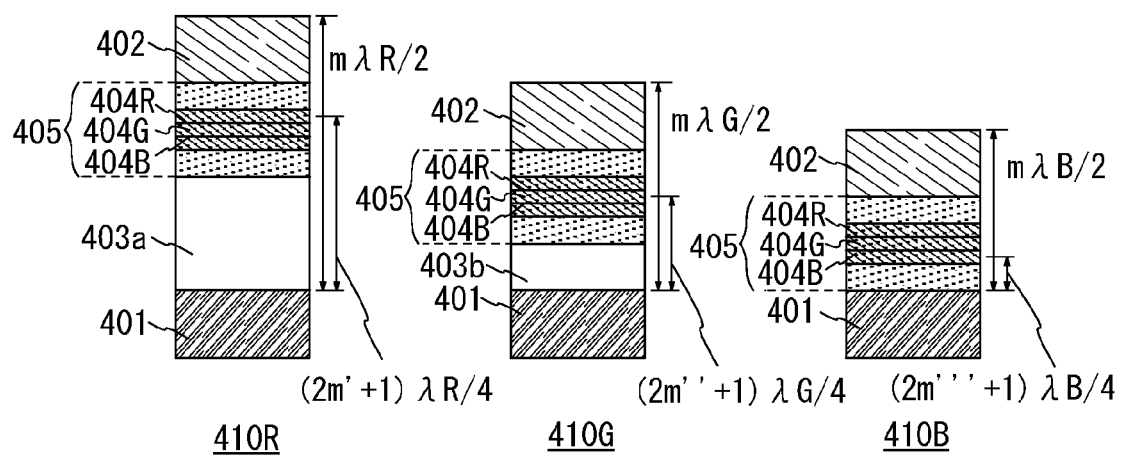
FIG. 4 illustrates a light-emitting device.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least a light-emitting layer 404 serving as a light-emitting region and may further include a hole-injection layer, a hole-transport layer, an electron-transport layer, an electron-injection layer, a charge generation layer (E), and the like. Note that the carbazole compound of one embodiment of the present invention can be used for any of a hole-injection layer, a hole-transport layer, the light-emitting layer 404, and an electron-transport layer which are included in the EL layer 405.

In this embodiment, a light-emitting device is described which includes light-emitting elements (a first light-emitting element (R) 410R, a second light-emitting element (G) 410G, and a third light-emitting element (B) 410B) having different structures as illustrated in FIG. 4.

The first light-emitting element (R) 410R has a structure in which a first transparent conductive layer 403a; an EL layer 405 including a first light-emitting layer (B) 404B, a second light-emitting layer (G) 404G and a third light-emitting layer (R) 404R in part; and a semi-transmissive and semi-reflective electrode 402 are sequentially stacked over a reflective electrode 401. The second light-emitting element (G) 410G has a structure in which a second transparent conductive layer 403b, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light ($\lambda_B$) having a peak in a wavelength range from 420 nm to 480 nm. The second light-emitting layer (G) 404G emits light ($\lambda_G$) having a peak in a wavelength range from 500 nm to 550 nm. The third light-emitting layer (R) 404R emits light ($\lambda_R$) having a peak in a wavelength range from 600 nm to 760 nm. Thus, in each of the light-emitting elements (the first light-emitting element (R) 410R, the second light-emitting element (G) 410G, and the third light-emitting element (B) 410B), light emitted from the first light-emitting layer (B) 404B, light emitted from the second light-emitting layer (G) 404G and light emitted from the third light-emitting layer (R) 404R overlap with each other; accordingly, light having a broad emission spectrum that covers a visible light range can be emitted. Note that the above wavelengths satisfy the relation of $\lambda_B < \lambda_G < \lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1 \times 10^{-2}$ Ωcm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1 \times 10^{-2}$ Ωcm or lower is used.

In this embodiment, the thicknesses of the transparent conductive layers (the first transparent conductive layer 403a and the second transparent conductive layer 403b) provided in the first light-emitting element (R) 410R and the second light-emitting element (G) 410G respectively, are varied between the light-emitting elements, whereby the light-emitting elements differ in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be enhanced while light with a wavelength that is not resonated therebetween can be attenuated. Thus, when the elements differ in the optical path length from the reflective electrode 401 to the semi-transmissive and semi-reflective electrode 402, light with different wavelengths can be extracted.

Note that the optical path length (also referred to as optical distance) is expressed as a product of an actual distance and a refractive index, and in this embodiment, is a product of an actual thickness and n (refractive index). That is, an optical path length=actual thickness×n.

Further, the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light $(\lambda_R)$ emitted from the third light-emitting layer (R) 404R included in the EL layer 405 is mainly extracted from the first light-emitting element (R) 410R, the light $(\lambda_G)$ emitted from the second light-emitting layer (G) 404G included in the EL layer 405 is mainly extracted from the second light-emitting element (G) 410G, and the light $(\lambda_B)$ emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is assumed that the above effect can be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness $((2m'+1)\lambda_R/4$, where m' is a natural number); thus, light emitted from the third light-emitting layer (R) 404R can be amplified. Light (first reflected light) that is reflected by the reflective electrode 401 of the light emitted from the third light-emitting layer (R) 404R interferes with light (first incident light) that directly enters the semi-transmissive and semi-reflective electrode 402 from the third light-emitting layer (R) 404R. Therefore, by adjusting the optical path length from the reflective electrode 401 to the third light-emitting layer (R) 404R to the desired value $((2m'+1)\lambda_R/4$, where m' is a natural number), the phases of the first reflected light and the first incident light can be aligned with each other and the light emitted from the third light-emitting layer (R) 404R can be amplified.

Note that strictly speaking, the optical path length from the reflective electrode 401 to the third light-emitting layer (R) 404R can be the optical path length from a reflection region in the reflective electrode 401 to a light-emitting region in the third light-emitting layer (R) 404R However, it is difficult to precisely determine the positions of the reflection region in the reflective electrode 401 and the light-emitting region in the third light-emitting layer (R) 404R; therefore, it is assumed that the above effect can be sufficiently obtained wherever the reflection region and the light-emitting region may be set in the reflective electrode 401 and the third light-emitting layer (R) 404R, respectively.

Next, in the second light-emitting element (G) 410G the optical path length from the reflective electrode 401 to the second light-emitting layer (G) 404G is adjusted to a desired thickness $((2m''+1)\lambda_G/4$, where m'' is a natural number); thus, light emitted from the second light-emitting layer (G) 404G can be amplified. Light (second reflected light) that is reflected by the reflective electrode 401 of the light emitted from the second light-emitting layer (G) 404G interferes with light (second incident light) that directly enters the semi-transmissive and semi-reflective electrode 402 from the second light-emitting layer (G) 404G Therefore, by adjusting the optical path length from the reflective electrode 401 to the second light-emitting layer (G) 404G to the desired value $((2m''+1)\lambda_G/4$, where m'' is a natural number), the phases of the second reflected light and the second incident light can be aligned with each other and the light emitted from the second light-emitting layer (G) 404G can be amplified.

Note that strictly speaking, the optical path length from the reflective electrode 401 to the second light-emitting layer (G) 404G can be the optical path length from a reflection region in the reflective electrode 401 to a light-emitting region in the second light-emitting layer (G) 404G However, it is difficult to precisely determine the positions of the reflection region in the reflective electrode 401 and the light-emitting region in the second light-emitting layer (G) 404G; therefore, it is assumed that the above effect can be sufficiently obtained wherever the reflection region and the light-emitting region may be set in the reflective electrode 401 and the second light-emitting layer (G) 404G, respectively.

Next, in the third light-emitting element (B) 410B, the optical path length from the reflective electrode 401 to the first light-emitting layer (B) 404B is adjusted to a desired thickness $((2m'''+1)\lambda_B/4$, where m''' is a natural number); thus, light emitted from the first light-emitting layer (B) 404B can be amplified. Light (third reflected light) that is reflected by the reflective electrode 401 of the light emitted from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value $((2m'''+1)\lambda_B/4$, where m''' is a natural number), the phases of the third reflected light and the third incident light can be aligned with each other and the light emitted from the first light-emitting layer (B) 404B can be amplified.

Note that strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B; therefore, it is assumed that the above effect can be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a charge generation layer is interposed between a plurality of EL layers in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layers, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

Embodiment 6

In this embodiment, a light-emitting device including a light-emitting element in which the carbazole compound of one embodiment of the present invention is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
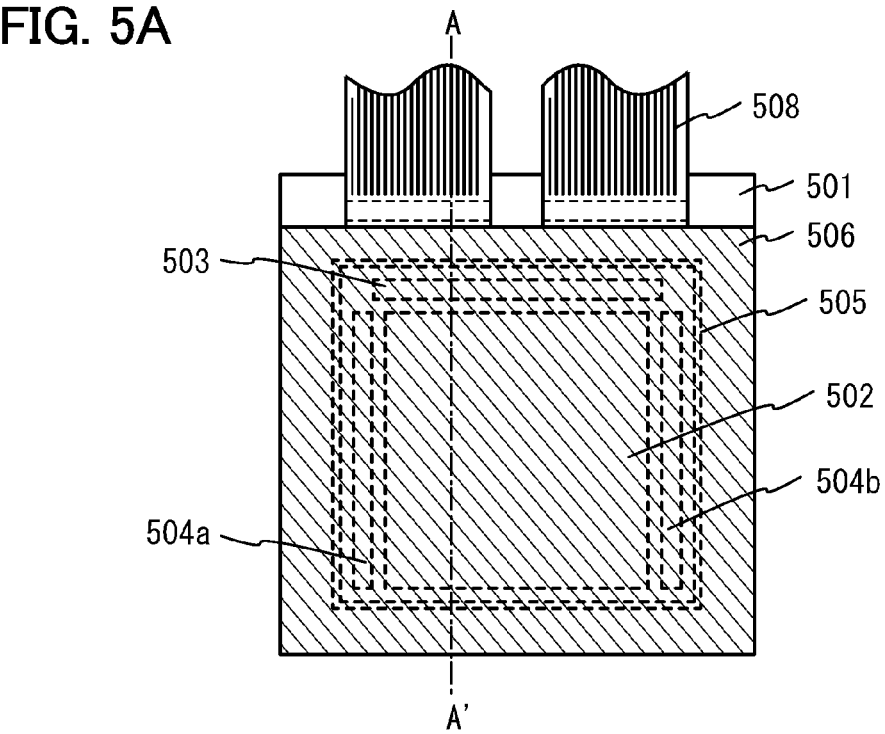
FIGS. 5A and 5B illustrate a light-emitting device.
Figure 5B:
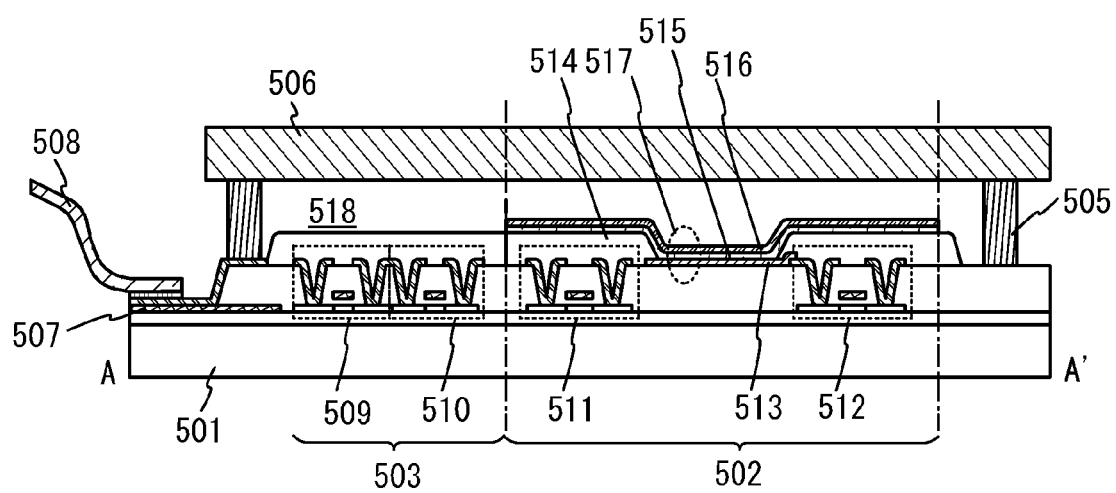

Note that FIG. 5A is a top view illustrating a light-emitting device and FIG. 5B is a cross-sectional view taken along the chain line A-A' in FIG. 5A. The active matrix light-emitting device according to this embodiment includes a pixel portion 502 provided over an element substrate 501, a driver circuit portion (a source line driver circuit) 503, and driver circuit portions (gate line driver circuits) 504a and 504b. The pixel portion 502, the driver circuit portion 503, and the driver circuit portions 504a and 504b are sealed between the element substrate 501 and the sealing substrate 506 with a sealant 505.

In addition, there is provided a lead wiring 507 over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portions 504a and 504b. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and the driver circuit can be formed outside, not over the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 μm to 3 μm) at the upper end portion. Note that the insulator 514 can be formed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode (cathode) 516 are stacked over the first electrode (anode) 513. In the EL layer 515, at least a light-emitting layer is provided. Further, in the EL layer 515, a hole-injection layer, a hole-transport layer, an electron-transport layer, an electron-injection layer, a charge generation layer, and the like can be provided as appropriate in addition to the light-emitting layer. Note that the carbazole compound of one embodiment of the present invention can be applied to the light-emitting layer, the hole-injection layer, the hole-transport layer, or the electron-transport layer.

A light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to an FPC 508 which is an external input terminal.

Although the cross-sectional view of FIG. 5B illustrates only one light-emitting element 517, a plurality of light-emitting elements are arranged in matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), poly (vinyl fluoride) (PVF), a polyester, an acrylic resin, or the like can be used.

As described above, an active matrix light-emitting device can be obtained.

Note that the structure described in this embodiment can be combined as appropriate with any of the structures described in the other embodiments.

Embodiment 7

In this embodiment, examples of a variety of electronic devices which are completed using a light-emitting device will be described with reference to FIGS. 6A to 6D. The light-emitting device is fabricated using a light-emitting element that includes the carbazole compound of one embodiment of the present invention.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 6A to 6D.

Figure 6A:
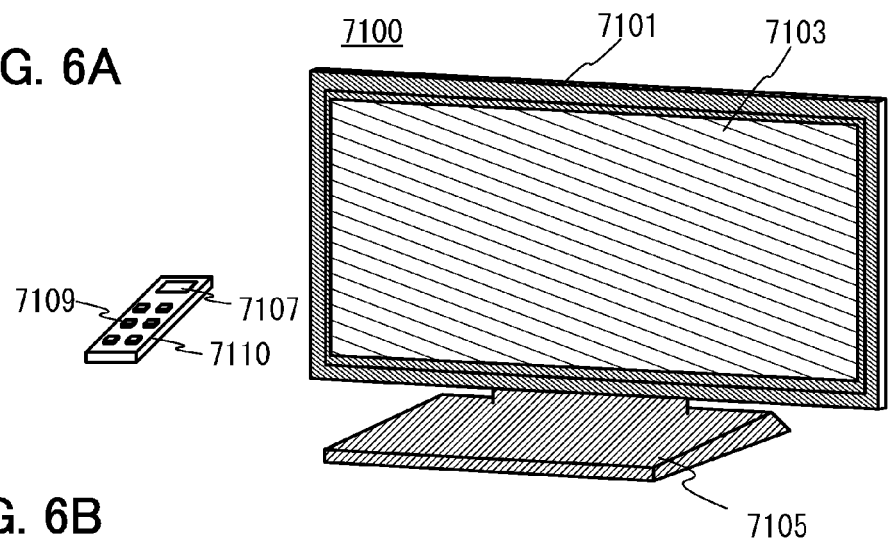
FIGS. 6A to 6D illustrate electronic devices.

FIG. 6A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 6B:
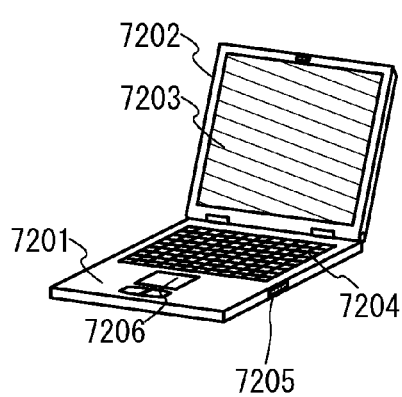

FIG. 6B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

Figure 6C:
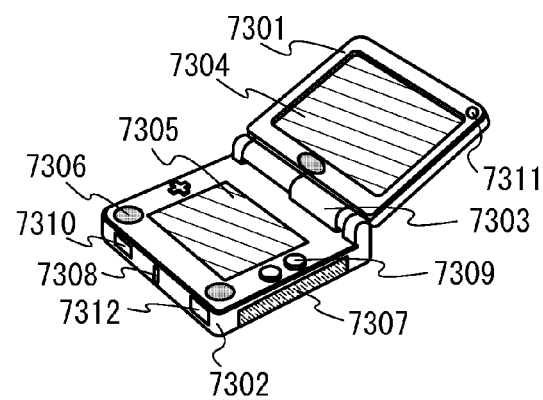

FIG. 6C illustrates a portable game machine having two housings, a housing 7301 and a housing 7302, which are connected with a joint portion 7303 so that the portable game machine can be opened or folded. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the light-emitting device is used for at least one of the display portion 7304 and the display portion 7305, and may include other accessories as appropriate. The portable game machine illustrated in FIG. 6C has a function of reading out a program or data stored in a storage medium to display it on the display portion, and a function of sharing information with another portable game machine by wireless communication. The portable game machine illustrated in FIG. 6C can have a variety of functions without limitation to the above.

Figure 6D:
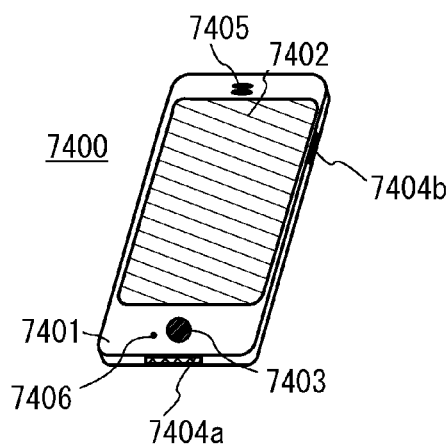

FIG. 6D illustrates an example of a mobile phone. A mobile phone 7400 is provided with a display portion 7402 incorporated in a housing 7401, an operation button 7403, external connection ports 7404a and 7404b, a speaker 7405, a microphone 7406, and the like. Note that the mobile phone 7400 is manufactured using the light-emitting device for the display portion 7402.

When the display portion 7402 of the mobile phone 7400 illustrated in FIG. 6D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by sensing the orientation of the mobile phone 7400 (whether the mobile phone is placed horizontally or vertically for a landscape mode or a portrait mode).

The screen modes are switched by touching the display portion 7402 or operating the operation button 7403 of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

As described above, the electronic devices can be obtained by the use of the light-emitting device according to one embodiment of the present invention. The light-emitting device has a remarkably wide application range, and can be applied to electronic devices in a variety of fields.

Note that the structure described in this embodiment can be combined as appropriate with any of the structures described in the other embodiments.

Embodiment 8

In this embodiment, examples of lighting devices which are completed using a light-emitting device will be described with reference to FIG. 7. The light-emitting device is fabricated using a light-emitting element that includes the carbazole compound of one embodiment of the present invention.

Figure 7:
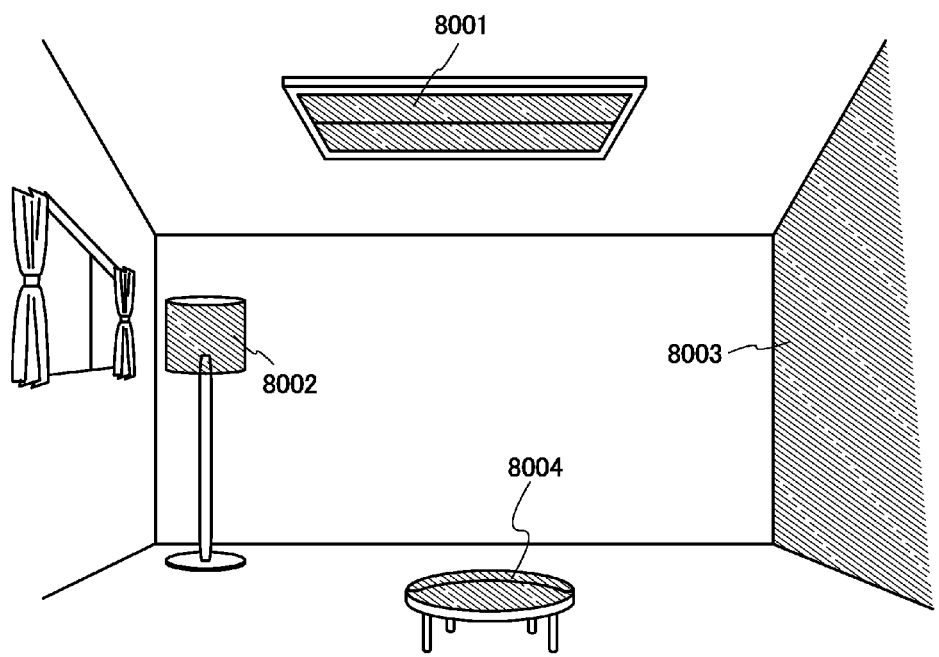
FIG. 7 illustrates lighting devices.

FIG. 7 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

Note that the carbazole compound of one embodiment of the present invention can be used in an organic thin film solar cell. More specifically, the carbazole compound can be used in a carrier-transport layer or a carrier-injection layer since the carbazole compound has a carrier-transport property. In addition, a mixed layer of the carbazole compound and an acceptor substance can be used as a charge generation layer. The carbazole compound can be photoexcited and hence can be used for a power generation layer.

Example 1

Synthesis Example 1

In this example, a method of synthesizing 3-[3,6-di(9H-carbazol-9-yl)-9H-carbazol-9-yl]pyridine (abbreviation: Cz2CzPy), which is one embodiment of the carbazole compound of the present invention represented by Structural Formula (100) in Embodiment 1, is described. The structure of Cz2CzPy (abbreviation) is shown below.

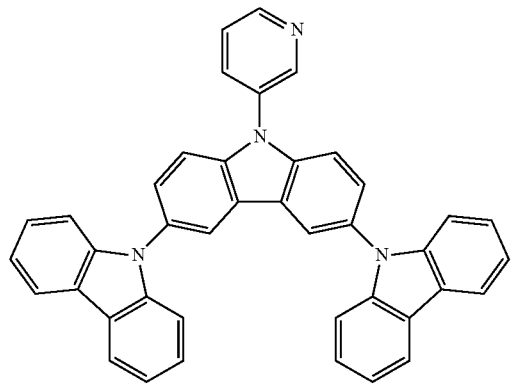

(100)

Synthesis of 3-[3,6-Di(9H-carbazol-9-yl)-9H-carbazol-9-yl]pyridine (Abbreviation: Cz2CzPy)

In a 200-mL three-neck flask, a mixture including 1.6 g (4.0 mmol) of 3-(3,6-dibromo-9H-carbazol-9-yl)pyridine, 1.7 g (10 mmol) of carbazole, 190 mg (1.0 mmol) of copper(I) iodide, 530 mg (2.0 mmol) of 18-crown-6-ether, 2.8 g (20 mmol) of potassium carbonate, and 20 mL of 1,3-dimethyl-3,4,5,6-tetrahydro-2(1H)-pyrimidinone (abbreviation: DMPU) was stirred under a nitrogen atmosphere at 180° C. for 6 hours to cause a reaction.

After the reaction, water was added to this reaction mixture and filtration was performed. Methanol was added to an obtained residue and ultrasonic cleaning was performed. The residue was collected and dried; then, toluene was added and the mixture was stirred while being heated, and then filtered. An obtained filtrate was purified by silica gel column chromatography (with a developing solvent containing toluene and chloroform in a 2:1 ratio). A fraction obtained here was concentrated. Acetone and methanol were added and ultrasonic cleaning was performed. The mixture was then dried, so that an objective substance was obtained as 2.2 g of white powder at a yield of 96%.

A synthesis scheme of the above synthesis method is illustrated in (A-1) below.

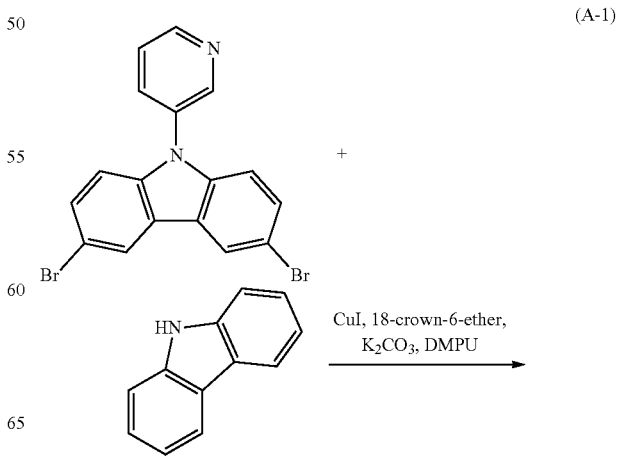

(A-1)

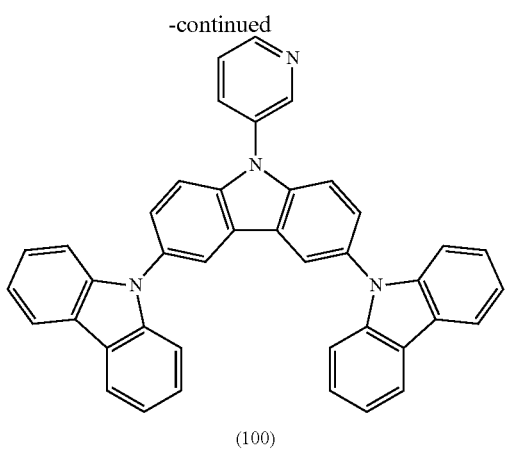

(100)

Note that the Rf values of the objective substance, 3-(3,6-dibromo-9H-carbazol-9-yl)pyridine, and carbazole were respectively 0.28, 0.28, and 0.72, which were obtained by silica gel thin layer chromatography (TLC) (with a developing solvent containing ethyl acetate and hexane in a 1:2 ratio).

Figure 8A:
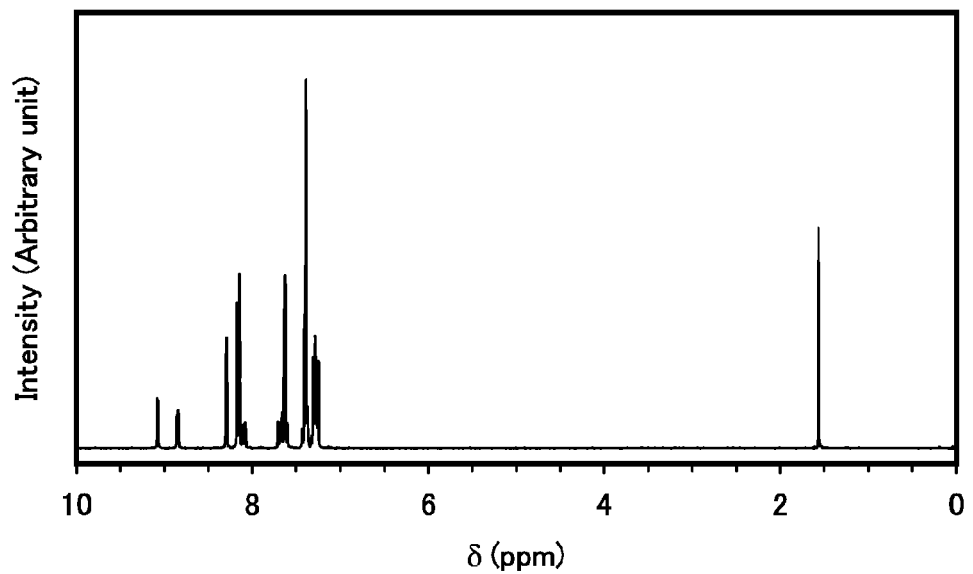
FIGS. 8A and 8B show $^1$H NMR charts of a carbazole compound represented by Structural Formula (100)
Figure 8B:
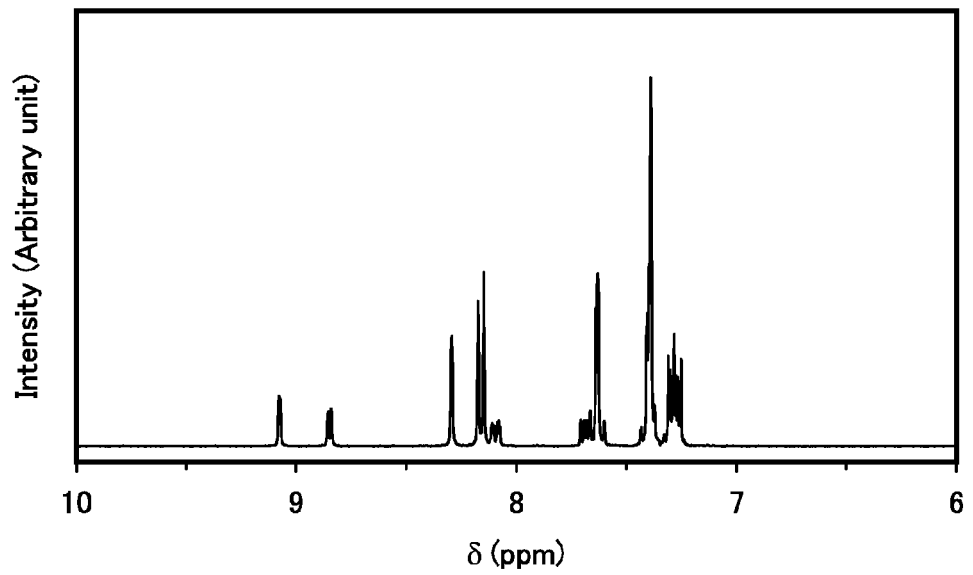

An analysis result by nuclear magnetic resonance spectrometry ($^1$H NMR) of the compound obtained by the above synthesis method is shown below. The $^1$H NMR charts are shown in FIGS. 8A and 8B. Note that FIG. 8B is an enlarged chart of FIG. 8A. The result revealed that 3-[3,6-di(9H-carbazol-9-yl)-9H-carbazol-9-yl]pyridine (abbreviation: Cz2CzPy), which is one embodiment of the carbazole compound of the present invention represented by Structural Formula (100) above, was obtained.

$^1$H NMR (CDCl$_3$, 300 MHz): δ (ppm)=7.25-7.31 (m, 4H), 7.37-7.41 (m, 8H), 7.60-7.71 (m, 5H), 8.08-8.11 (m, 1H), 8.16 (d, J=7.8 Hz, 4H), 8.29 (d, J=0.9 Hz, 2H), 8.85 (dd, J=1.6 Hz, 4.2 Hz, 1H), 8.08 (d, J=1.8 Hz, 1H).

Next, 3-[3,6-di(9H-carbazol-9-yl)-9H-carbazol-9-yl]pyridine (abbreviation: Cz2CzPy) obtained in this example was analyzed by liquid chromatography mass spectrometry (LC/MS).

In the analysis by LC/MS, liquid chromatography (LC) separation was carried out with Acquity UPLC (manufactured by Waters Corporation), and mass spectrometry (MS) analysis was carried out with Xevo G2 T of MS (manufactured by Waters Corporation). An Acquity UPLC BEH C8 column (2.1 mm×100 mm, 1.7 μm) was used in the LC separation, where a column temperature was 40° C. Acetonitrile was used for Mobile Phase A and a 0.1% formic acid aqueous solution was used for Mobile Phase B. A solution including the sample was prepared in such a manner that Cz2CzPy (abbreviation) was dissolved in toluene at a given concentration and the mixture was diluted with acetonitrile. The injection amount of the solution was 5.0 μL.

In the LC separation, a gradient method, in which composition of mobile phases is changed, was employed; the composition ratio of Mobile Phase A to Mobile Phase B was 60 to 40 for 0 minutes to 1 minute after the measurement started, and then the composition was changed, so that the ratio of Mobile Phase A to Mobile Phase B in the 10th minute was 95 to 5. The composition ratio was changed linearly.

In the MS analysis, ionization was carried out by an electrospray ionization (ESI) method. Capillary voltage and sample cone voltage were set to 3.0 kV and 30 V, respectively. Detection was performed in a positive mode (positive ion). A mass range for the measurement was m/z 100-1200.

A component which underwent the separation and the ionization under the above-mentioned conditions was collided with an argon gas in a collision cell to dissociate into product ions. Energy (collision energy) for the collision with argon was 70 eV. The results of MS analysis are shown in FIG. 22.

Figure 22:
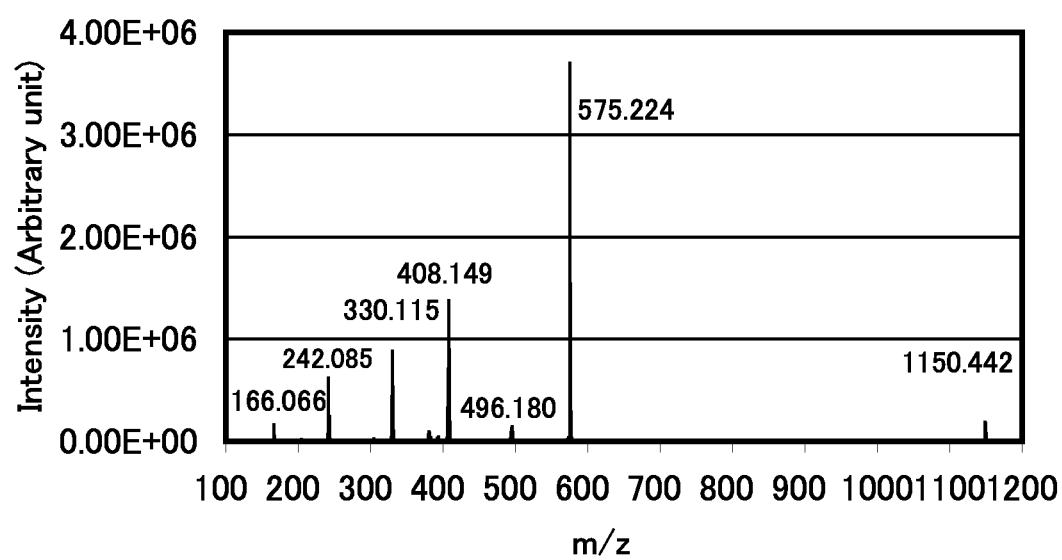
FIG. 22 shows results of LC/MS measurement of a carbazole compound represented by Structural Formula (100)

The results in FIG. 22 show that product ions of partial skeletons of Cz2CzPy (abbreviation), which is a heterocyclic compound of one embodiment of the present invention represented by Structural Formula (100), are detected mainly around m/z 496, m/z 408, m/z 330, m/z 242, and m/z 166. Characteristically derived from Cz2CzPy (abbreviation), the results shown in FIG. 22 can be regarded as important data in identification of Cz2CzPy (abbreviation) contained in a mixture.

Figure 23:
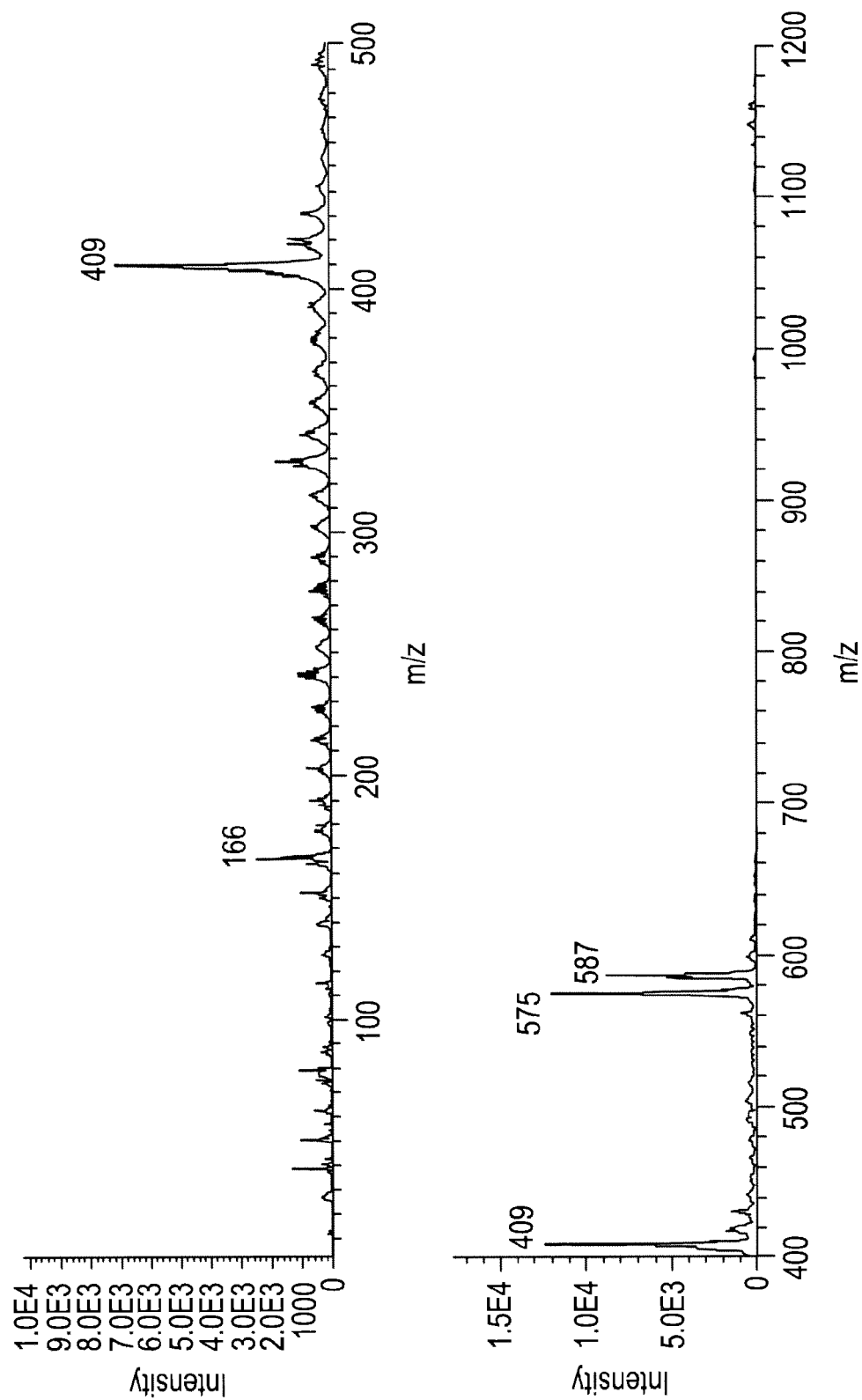
FIG. 23 shows results of TOF-SIMS (positive ion) measurement of a carbazole compound represented by Structural Formula (100)
Figure 24:
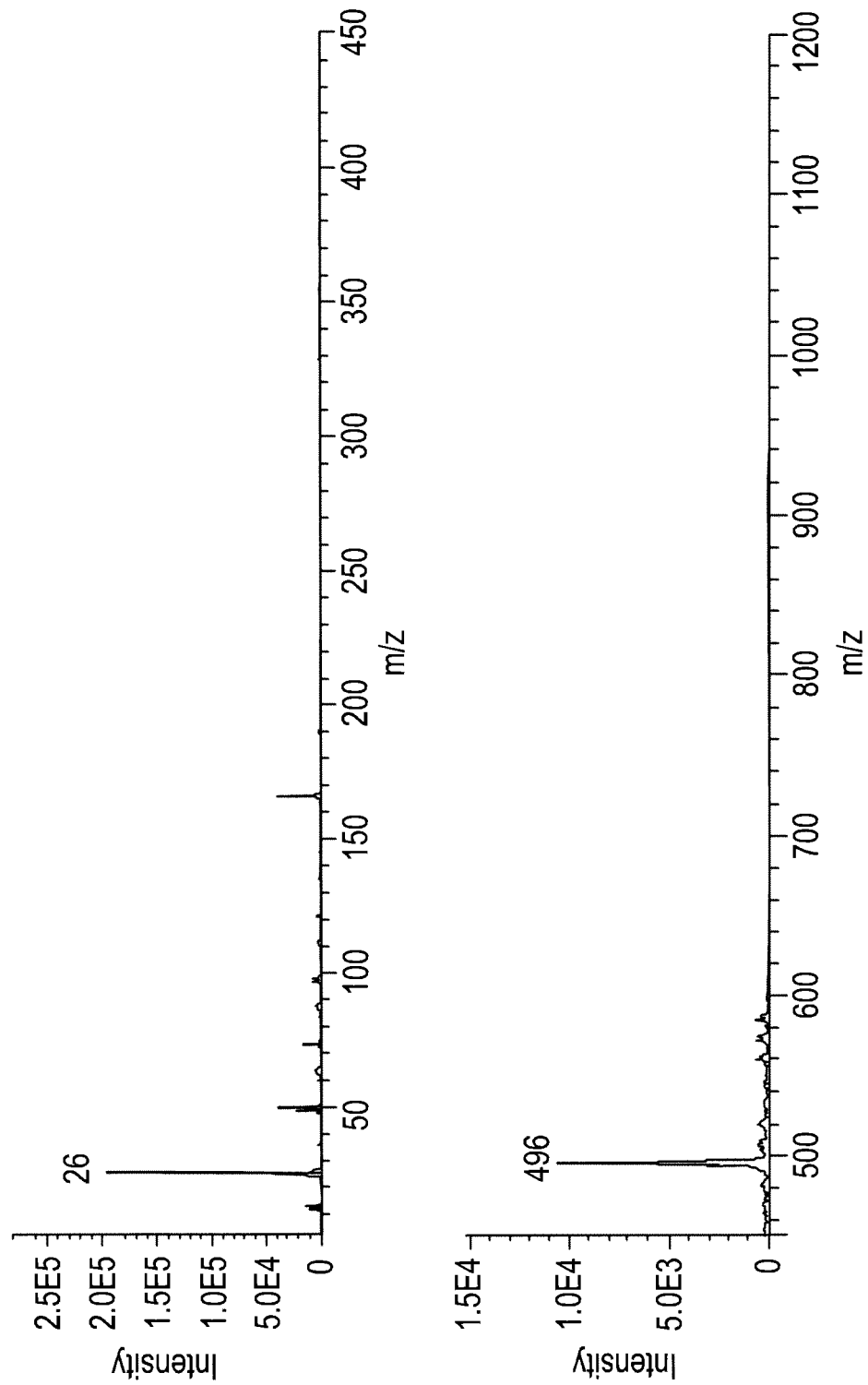
FIG. 24 shows results of TOF-SIMS (negative ion) measurement of a carbazole compound represented by Structural Formula (100).

Cz2CzPy (abbreviation), which is one embodiment of the present invention, was measured with a time-of-flight secondary ion mass spectrometer (TOF-SIMS); obtained qualitative spectra are shown in FIG. 23 (positive ion) and FIG. 24 (negative ion).

TOF.SIMS 5 (manufactured by ION-TOF GmbH) was used, where Bi$_3^{++}$ was used as a primary ion source. Note that irradiation with the primary ions was performed in a pulsed manner with a pulse width of 7 nm to 12 nm. The irradiation amount was greater than or equal to 8.2×10$^{10}$ ions/cm$^2$ and less than or equal to 6.7×10$^{11}$ ions/cm$^2$ (less than or equal to 1×10$^{12}$ ions/cm$^2$), acceleration voltage was 25 keV, and a current value was 0.2 pA. A powder of Cz2CzPy (abbreviation) was the sample used for the measurement.

The results of analysis by TOF-SIMS (positive ion) in FIG. 23 show that product ions of the partial skeletons of Cz2CzPy (abbreviation) (m/z 574.22), which is the heterocyclic compound of one embodiment of the present invention represented by Structural Formula (100), are detected mainly around m/z 409 and m/z 166. Here, the expression "around" is used in consideration of measurement errors. Since the product ions detected here are similar to the product ions of the partial skeletons of Cz2CzPy (abbreviation) in FIG. 22, which were detected by the MS analysis (positive ion), the results of the measurement by TOF-SIMS which are shown in FIG. 23 can also be regarded as important data in identification of Cz2CzPy (abbreviation) contained in a mixture.

The results of analysis by TOF-SIMS (negative ion) in FIG. 24 show that a product ion of the partial skeleton of Cz2CzPy (abbreviation) (m/z 574.22), which is the heterocyclic compound of one embodiment of the present invention represented by Structural Formula (100), is detected mainly around m/z 496. Similarly to the above, these results can also be regarded as important data in identification of Cz2CzPy (abbreviation) contained in a mixture.

Next, ultraviolet-visible absorption spectra (hereinafter, simply referred to as "absorption spectra") and emission spectra of Cz2CzPy (abbreviation) were measured. The absorption spectra were measured using an ultraviolet-visible light spectrophotometer (V550 type manufactured by Japan Spectroscopy Corporation). The emission spectra were measured using a fluorescence spectrophotometer (FS920 manufactured by Hamamatsu Photonics Corporation). The absorption spectra and the emission spectra of a toluene solution of Cz2CzPy (abbreviation) and a thin film of Cz2CzPy (abbreviation) were measured. Put in a quartz cell, the toluene solution was subjected to the measurement at room temperature. As for the thin film, the thin film which was deposited on a quartz substrate by evaporation was used. In order to obtain the absorption spectrum of the thin film, an absorption spectrum of quartz was subtracted from an absorption spectrum of the thin film and quartz.

Figure 9A:
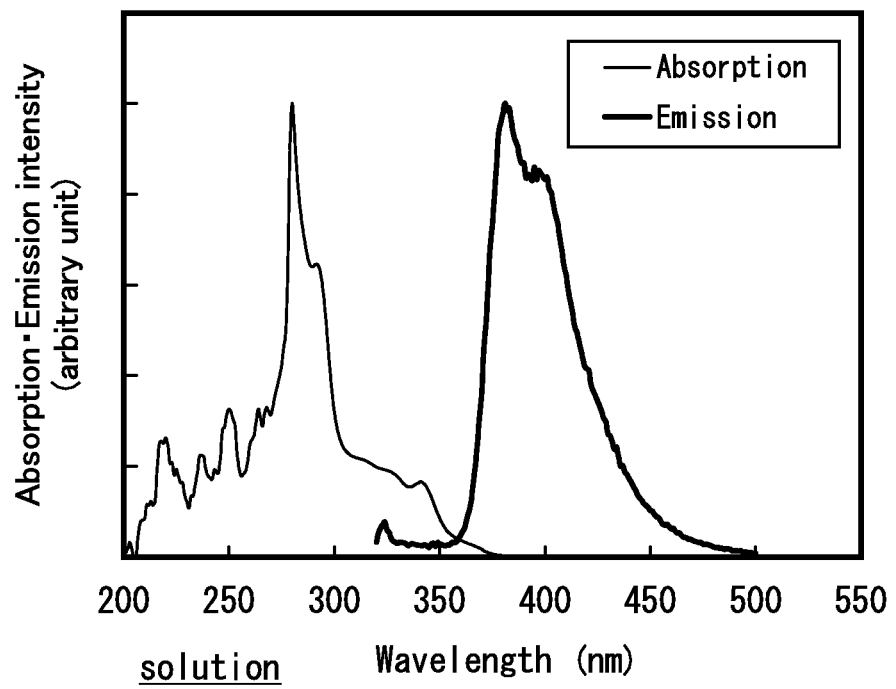
FIGS. 9A and 9B show ultraviolet-visible absorption spectra and emission spectra of a carbazole compound represented by Structural Formula (100)
Figure 9B:
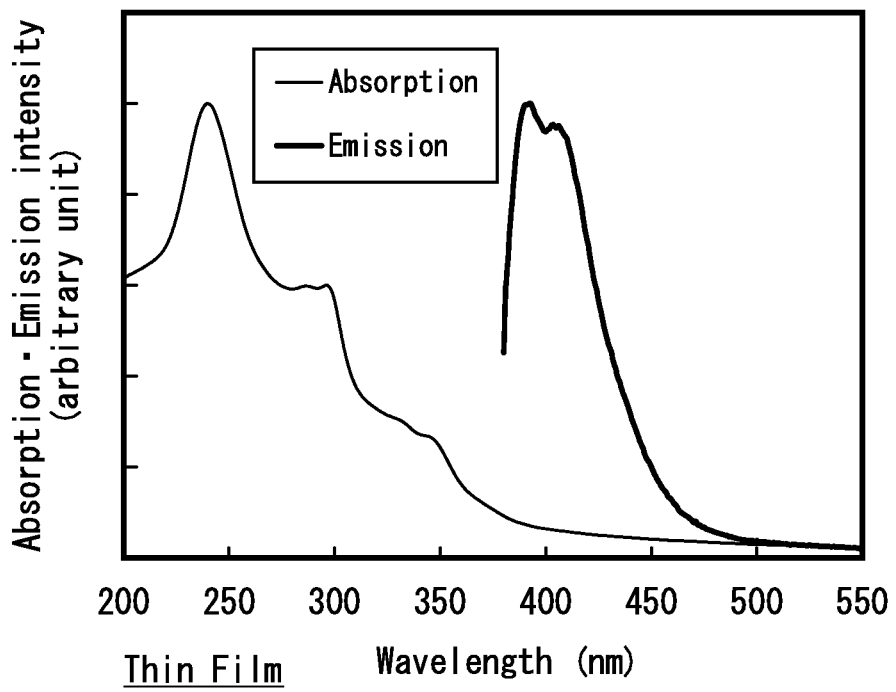

FIGS. 9A and 9B show measurement results of the absorption spectra and emission spectra. FIG. 9A shows the measurement results of the toluene solution of Cz2CzPy (abbreviation). FIG. 9B shows the measurement results of the thin film of Cz2CzPy (abbreviation). In each of FIGS. 9A and 9B, the horizontal axis represents wavelength (nm) and the vertical axis represents absorption intensity (arbitrary unit) or emission intensity (arbitrary unit). In each of FIGS. 9A and 9B, two solid lines are shown; a thin line represents the absorption spectrum, and a thick line represents the emission spectrum.

In the case of the toluene solution of Cz2CzPy (abbreviation), an absorption peak is observed at around 342 nm as shown in FIG. 9A. In the case of the thin film of Cz2CzPy (abbreviation), an absorption peak is observed at around 365 nm as shown in FIG. 9B.

Further, in the case of the toluene solution of Cz2CzPy (abbreviation), the maximum emission wavelengths are 381 nm and 398 nm (excitation wavelength: 295 nm) as shown in FIG. 9A. In the case of the thin film of Cz2CzPy (abbreviation), the maximum emission wavelengths are 406 nm and 392 nm (excitation wavelength: 367 nm) as shown in FIG. 9B.

As described above, Cz2CzPy (abbreviation) was found to emit blue light with high color purity and accordingly can be used for a blue-light-emitting material.

The HOMO level and the LUMO level of Cz2CzPy (abbreviation) were measured using the thin film with a photoelectron spectrometer (AC-2, manufactured by Riken Keiki Co., Ltd.) in the air and the HOMO level of Cz2CzPy was found to be −5.69 eV. The Tauc plot of the absorption spectrum of the thin film revealed that the absorption edge is 3.17 eV. Thus, the energy gap in the solid state was estimated to be 3.17 eV, which means that the LUMO level of Cz2CzPy is −2.52 eV.

Thus, it was found that the HOMO level of Cz2CzPy (abbreviation) is relatively low and the LUMO level thereof is high, which shows that Cz2CzPy has a wide band gap (Bg).

Further, the HOMO level and the LUMO level of Cz2CzPy (abbreviation) were measured using a solution by cyclic voltammetry (CV). An electrochemical analyzer (ALS model 600A or 600C, manufactured by BAS Inc.) was used for the CV measurement.

Further, as for the solution used for the CV measurement, dehydrated dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. A platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. The CV measurement was performed under the following conditions: room temperature (20° C. to 25° C.) and a scan rate of 0.1 V/sec. Note that the potential energy of the reference electrode with respect to the vacuum level was assumed to be −4.94 eV in this example.

On the assumption that the intermediate potential (the half-wave potential) between the oxidation peak potential E$_{pa}$ and the reduction peak potential E$_{pc}$ which are obtained in the CV measurement corresponds to the HOMO level, the HOMO level of Cz2CzPy (abbreviation) was calculated to be −5.85 eV.

Example 2

Figure 10:
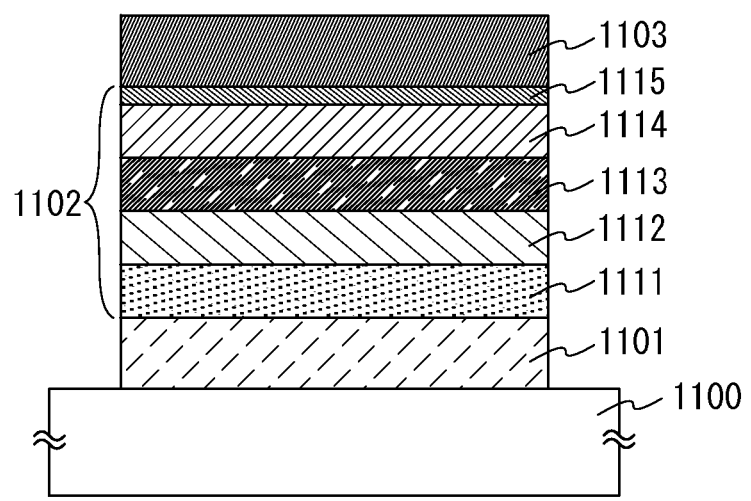
FIG. 10 illustrates a light-emitting element.

This example describes Light-emitting Element 1 and Comparative Light-emitting Element 1 which was fabricated for comparison; in Light-emitting Element 1, 3-[3,6-di(9H-carbazol-9-yl)-9H-carbazol-9-yl]pyridine (abbreviation: Cz2CzPy), one embodiment of the carbazole compound of the present invention represented by Structural Formula (100), is used in a hole-transport layer and part of a light-emitting layer. Note that structures of Light-emitting Element 1 and Comparative Light-emitting Element 1 are described with reference to FIG. 10. Chemical formulae of materials used in this example are shown below.

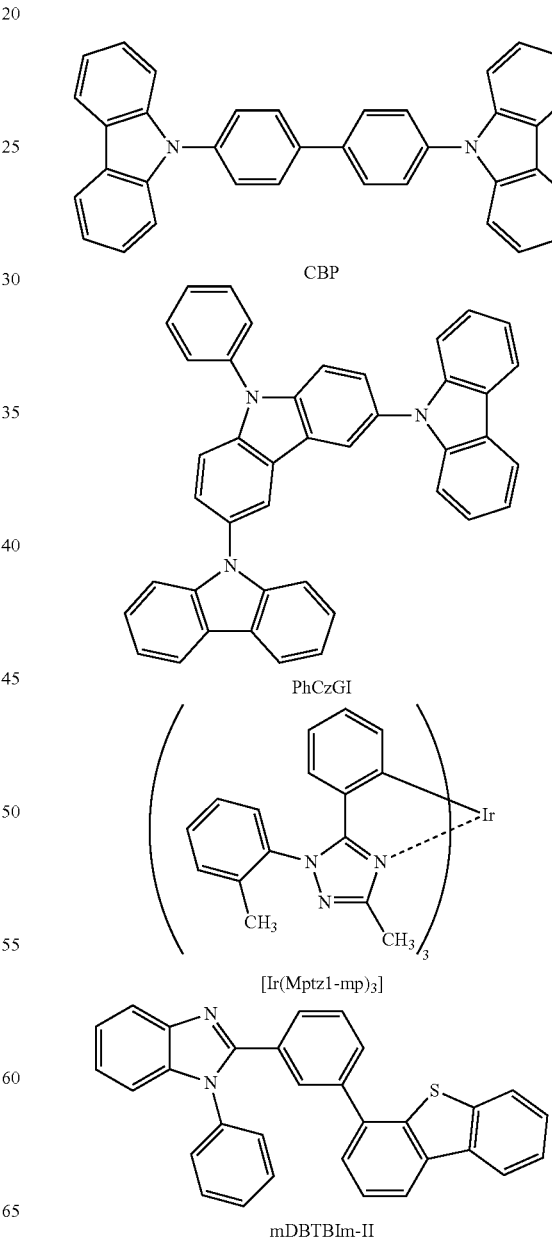

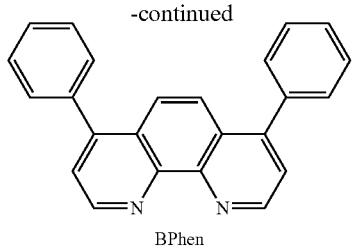

BPhen

Fabrication of Light-Emitting Element 1 and Comparative Light-Emitting Element 1

First, indium tin oxide containing silicon oxide (ITSO) was deposited over a glass substrate 1100 by a sputtering method, so that a first electrode 1101 which functions as an anode was formed. The thickness was 110 nm and the electrode area was 2 mm×2 mm.

Next, as pretreatment for forming the light-emitting element over the substrate 1100, the surface of the substrate was washed with water, baked at 200° C. for 1 hour, and subjected to UV ozone treatment for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that the surface of the substrate 1100 over which the first electrode 1101 was formed faced downward. In this example, a case will be described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After reducing the pressure of the vacuum evaporation apparatus to $10^{-4}$ Pa, 4,4'-di(N-carbazolyl)biphenyl (abbreviation: CBP) and molybdenum(VI) oxide were co-evaporated with a mass ratio of CBP (abbreviation) to molybdenum oxide being 4:2, whereby the hole-injection layer 1111 was formed over the first electrode 1101. The thickness of the hole-injection layer 1111 was 60 nm. Note that the co-evaporation is an evaporation method in which some different substances are evaporated from some different evaporation sources at the same time.

Then, 3-[3,6-di(9H-carbazol-9-yl)-9H-carbazol-9-yl]pyridine (abbreviation: Cz2CzPy) was deposited by evaporation to a thickness of 20 nm, so that the hole-transport layer 1112 was formed.

Next, the light-emitting layer 1113 was formed over the hole-transport layer 1112 in the following manner. First, 3-[3,6-di(9H-carbazol-9-yl)-9H-carbazol-9-yl]pyridine (abbreviation: Cz2CzPy) and tris[3-methyl-1-(2-methylphenyl)-5-phenyl-1H-1,2,4-triazolato]iridium(III) (abbreviation: [Ir(Mptz1-mp)$_3$]) were co-evaporated with a mass ratio of Cz2CzPy (abbreviation) to [Ir(Mptz1-mp)$_3$] (abbreviation) being 1:0.08 to form a 30-nm-thick film. Then, 2-[3-(dibenzothiophen-4-yl)phenyl]-1-phenyl-1H-benzimidazole (abbreviation: mDBTBIm-II) and [Ir(Mptz1-mp)$_3$] (abbreviation) were co-evaporated with a mass ratio of mDBTBIm-II (abbreviation) to [Ir(Mptz1-mp)$_3$] (abbreviation) being 1:0.08 to form a 10-nm-thick film. Thus, the light-emitting layer 1113 having a stacked structure was formed.

Then, bathophenanthroline (abbreviation: Bphen) was deposited by evaporation to a thickness of 15 nm over the light-emitting layer 1113, whereby the electron-transport layer 1114 was formed. Furthermore, lithium fluoride was then deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form a second electrode 1103 serving as a cathode; thus, Light-emitting Element 1 was obtained. Note that in all the above evaporation steps, evaporation was performed by a resistance-heating method.

Comparative Light-emitting Element 1 was fabricated for comparison with Light-emitting Element 1. Comparative Light-emitting Element 1 was fabricated in a similar manner to that of Light-emitting Element 1 except that the hole-transport layer 1112 was formed by depositing 3,6-di(9H-carbazol-9-yl)-9-phenyl-9H-carbazole (abbreviation: PhCzGI) by evaporation to a thickness of 20 nm, and that the first layer of the light-emitting layer which was on and in contact with the hole-transport layer 1112 was formed to a thickness of 30 nm by co-evaporation of 3,6-di(9H-carbazol-9-yl)-9-phenyl-9H-carbazole (abbreviation: PhCzGI) and tris[3-methyl-1-(2-methylphenyl)-5-phenyl-1H-1,2,4-triazolato]iridium(III) (abbreviation: [Ir(Mptz1-mp)$_3$]) with a mass ratio of PhCzGI (abbreviation) to [Ir(Mptz1-mp)$_3$] (abbreviation) being 1:0.08.

Element structures of Light-emitting Element 1 and Comparative Light-emitting Element 1 obtained as described above are shown in Table 1.

TABLE 1

| | First Electrode | Hole-injection Layer | Hole-transport Layer | Light-emitting Layer | | Electron-transport Layer | Electron-injection Layer | Second Electrode |
|---|---|---|---|---|---|---|---|---|
| Light-emitting Element 1 | ITSO (110 nm) | CBP:MoOx (4:2 60 nm) | Cz2CzPy (20 nm) | * | ** | Bphen (15 nm) | LiF (1 nm) | Al (200 nm) |
| Comparative Light-emitting Element 1 | ITSO (110 nm) | CBP:MoOx (4:2 60 nm) | PhCzGI (20 nm) | *** | **** | Bphen (15 nm) | LiF (1 nm) | Al (200 nm) |

\* Cz2CzPy: [Ir(Mptz1-mp)$_3$] (1:0.08 30 nm)

\*\* mDBTBIm-II: [Ir(Mptz1-mp)$_3$] (1:0.08 10 nm)

\*\*\* PhCzGI: [Ir(Mptz1-mp)$_3$] (1:0.08 30 nm)

\*\*\*\* mDBTBIm-II: [Ir(Mptz1-mp)$_3$] (1:0.08 10 nm)

Further, after fabrication, each of Light-emitting Element 1 and Comparative Light-emitting Element 1 was sealed in a glove box containing a nitrogen atmosphere so as not to be exposed to the air (specifically, a sealant was applied onto an outer edge of the element and heat treatment was performed at 80° C. for 1 hour at the time of sealing).

Operation Characteristics of Light-Emitting Element 1 and Comparative Light-Emitting Element 1

Operation characteristics of the fabricated Light-emitting Element 1 and Comparative Light-emitting Element 1 were measured. Note that the measurement was carried out at room temperature (under an atmosphere in which the temperature was kept at 25° C.).

Figure 11:
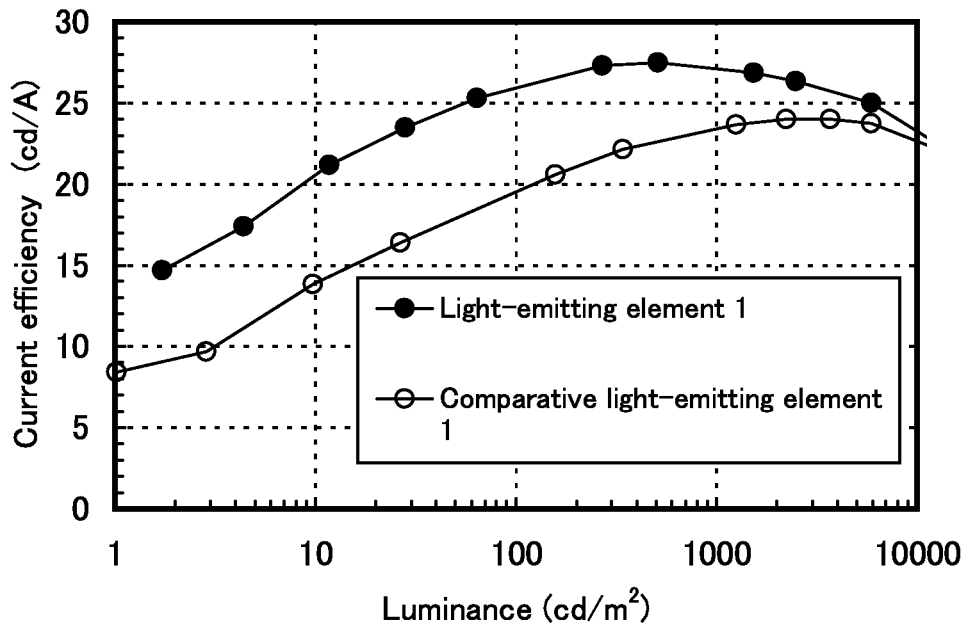
FIG. 11 shows luminance-current efficiency characteristics of Light-emitting Element 1 and Comparative Light-emitting Element 1.
Figure 12:
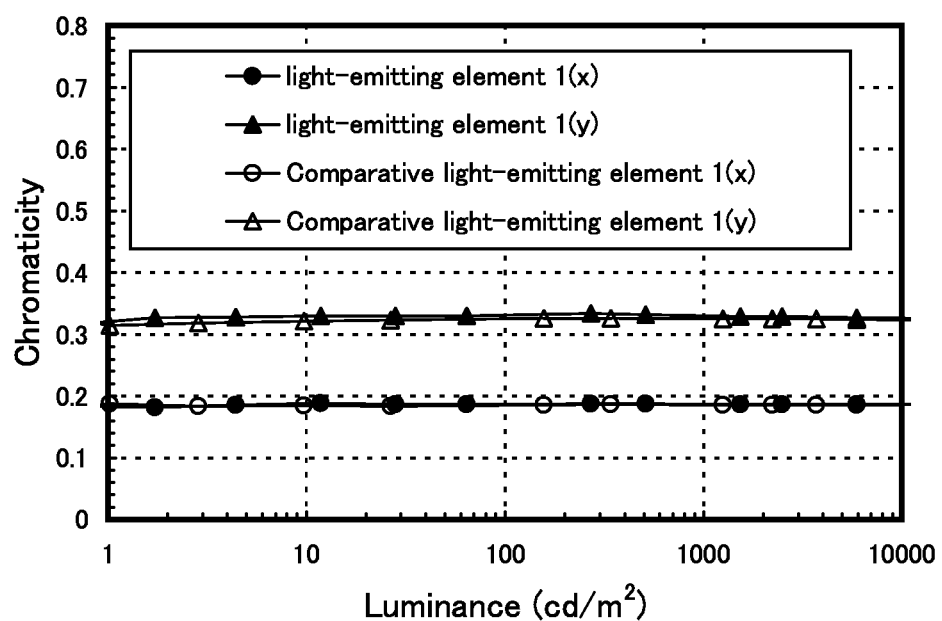
FIG. 12 shows luminance-chromaticity characteristics of Light-emitting Element 1 and Comparative Light-emitting Element 1.
Figure 13:
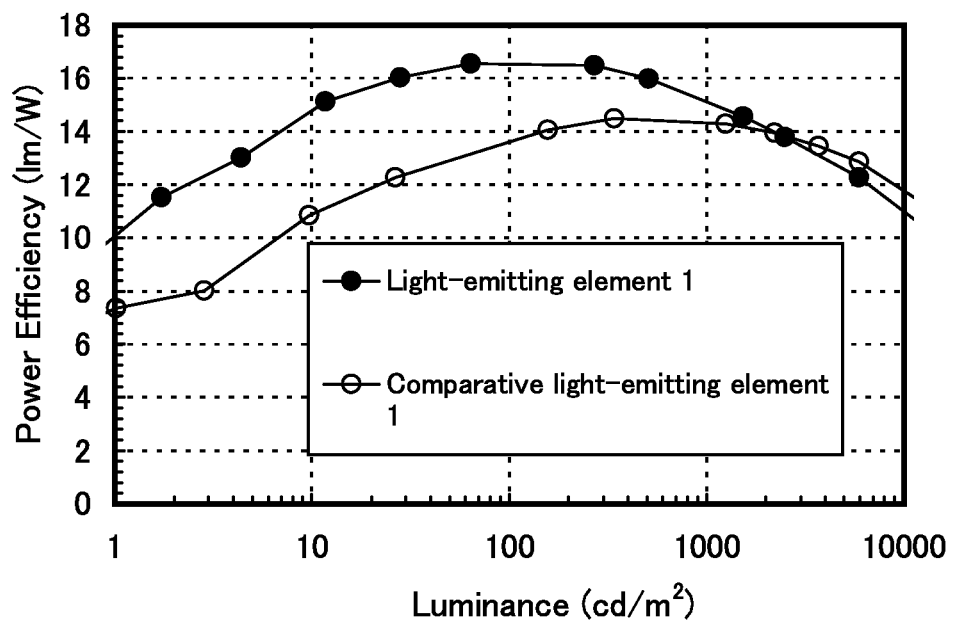
FIG. 13 shows luminance-power efficiency characteristics of Light-emitting Element 1 and Comparative Light-emitting Element 1.

The luminance-current efficiency characteristics of Light-emitting Element 1 and Comparative Light-emitting Element 1 are shown in FIG. 11. The luminance-chromaticity characteristics of Light-emitting Element 1 and Comparative Light-emitting Element 1 are shown in FIG. 12. The luminance-power efficiency characteristics of Light-emitting Element 1 and Comparative Light-emitting Element 1 are shown in FIG. 13.

FIG. 11 shows that Light-emitting Element 1 in which 3-[3,6-di(9H-carbazol-9-yl)-9H-carbazol-9-yl]pyridine (abbreviation: Cz2CzPy), one embodiment of the carbazole compound of the present invention, is used in the hole-transport layer and in part of the light-emitting layer as a host material has low power consumption and high efficiency. FIG. 12 shows that Light-emitting Element 1 has favorable carrier balance at any luminance.

Table 2 below shows initial values of main characteristics of Light-emitting Element 1 and Comparative Light-emitting Element 1 at a luminance of about 1000 cd/m².

TABLE 2

| | Voltage (V) | Current (mA) | Current Density (mA/cm²) | Chromaticity (x, y) | Luminance (cd/m²) | Current Efficiency (cd/A) | Power Efficiency (lm/W) |
|---|---|---|---|---|---|---|---|
| Light-emitting Element 1 | 5.4 | 0.07 | 1.9 | (0.19, 0.33) | 510 | 27 | 16 |
| Comparative Light-emitting Element 1 | 5.2 | 0.21 | 5.3 | (0.19, 0.32) | 1300 | 24 | 14 |

The above results in Table 2 also show that Light-emitting Element 1 fabricated in this example has high luminance and high current efficiency. Moreover, as for color purity, it can be found that the light-emitting element exhibits blue emission with excellent color purity.

Figure 14:
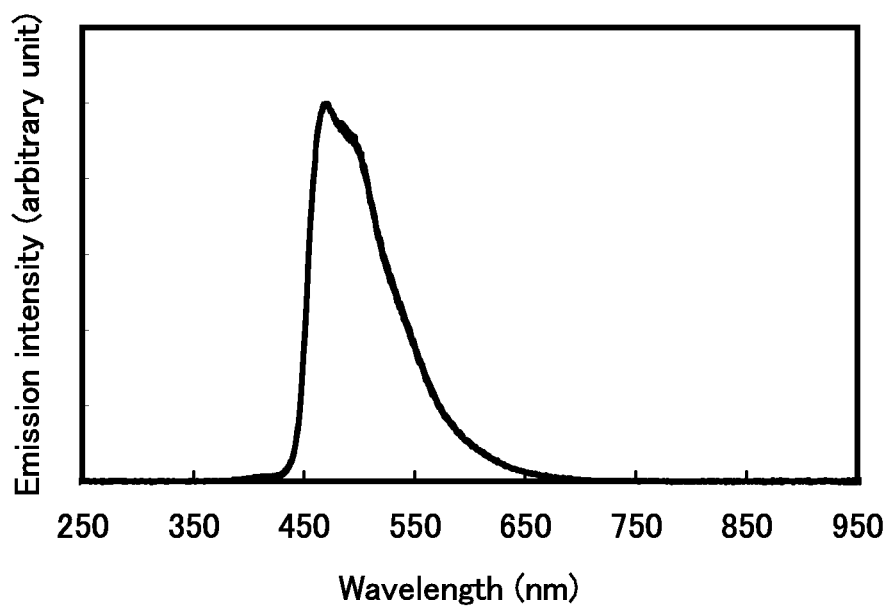
FIG. 14 shows emission spectra of Light-emitting Element 1 and Comparative Light-emitting Element 1.

FIG. 14 shows emission spectra when a current at a current density of 2.5 mA/cm² was supplied to Light-emitting Element 1 and Comparative Light-emitting Element 1. As shown in FIG. 14, each of the emission spectra of Light-emitting Element 1 and Comparative Light-emitting Element 1 has a peak at around 470 nm and it was indicated that the emission spectra were derived from emission of [Ir(Mptz1-mp)₃] (abbreviation) included in the light-emitting layer 1113.

The above results showed that 3-[3,6-di(9H-carbazol-9-yl)-9H-carbazol-9-yl]pyridine (abbreviation: Cz2CzPy), which is one embodiment of the carbazole compound of the present invention, has a high $T_1$ and can be used for a host material or a carrier-transport material in an element that emits phosphorescence (or fluorescence) in the visible region (having a longer wavelength than blue color).

Figure 15:
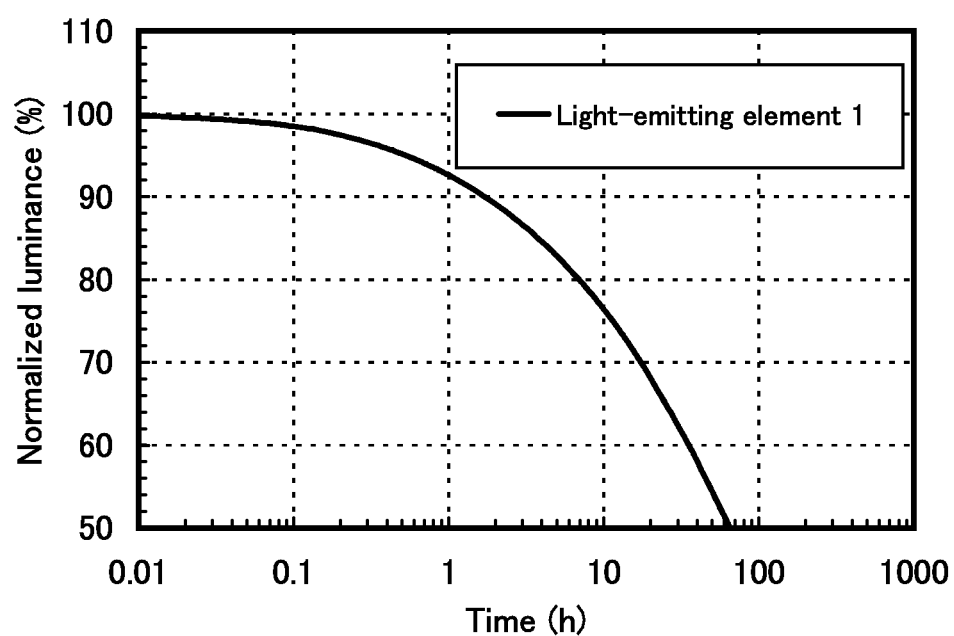
FIG. 15 shows reliability of Light-emitting Element 1.

Light-emitting Element 1 was subjected to a reliability test. Results of the reliability test are shown in FIG. 15. In FIG. 15, the vertical axis represents normalized luminance (%) with an initial luminance of 100% and the horizontal axis represents driving time (h) of the element. Note that in the reliability test, Light-emitting Element 1 was driven under the conditions where the initial luminance was set to 300 cd/m² and the current density was constant. Light-emitting Element 1 kept 75% of the initial luminance after 10 hours elapsed. This indicates high reliability of Light-emitting Element 1, in which the hole-transport layer and part of the light-emitting layer include Cz2CzPy (abbreviation), one embodiment of the carbazole compound of the present invention. In addition, it was confirmed that with the use of the carbazole compound of the present invention, a light-emitting element with a long lifetime can be obtained.

Example 3

This example describes Light-emitting Element 2 and Comparative Light-emitting Element 2 which was fabricated for comparison; in Light-emitting Element 2, 3-[3,6-di(9H-carbazol-9-yl)-9H-carbazol-9-yl]pyridine (abbreviation: Cz2CzPy), one embodiment of the carbazole compound of the present invention represented by Structural Formula (100), is used in part of a light-emitting layer. Note that FIG. 10, which is used for explanation in Example 1, is also used for explanation of Light-emitting Element 2 and Comparative Light-emitting Element 2 in this example. Chemical formulae of materials used in this example are shown below.

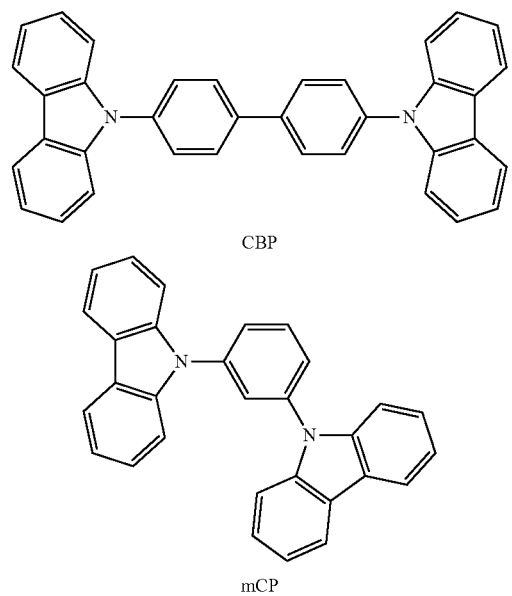

CBP mCP

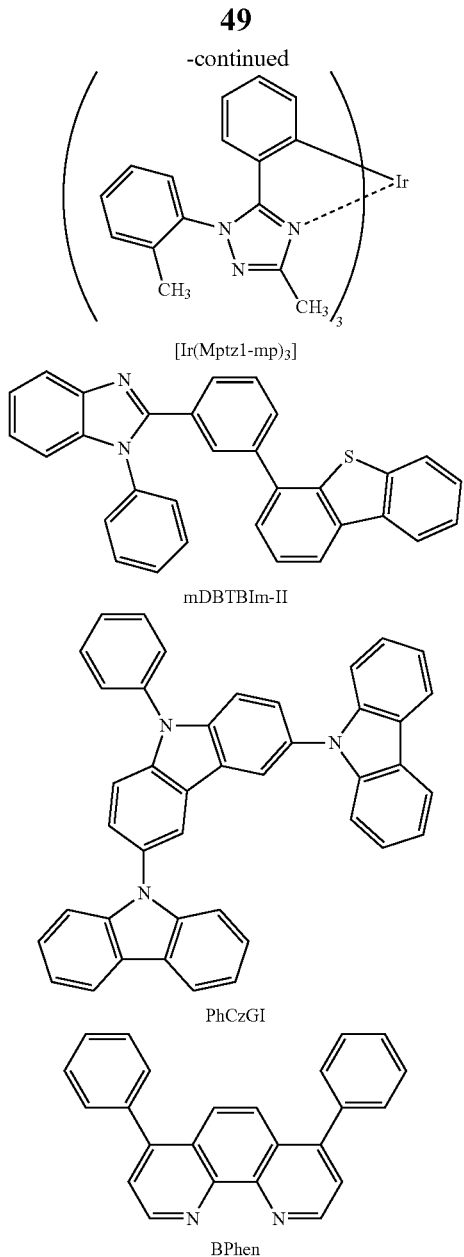

[Ir(Mptzl-mp)₃]

mDBTBIm-II

PhCzGI

BPhen

Fabrication of Light-Emitting Element 2 and Comparative Light-Emitting Element 2

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Next, as pretreatment for forming the light-emitting element over the substrate 1100, the surface of the substrate was washed with water, baked at 200° C. for 1 hour, and subjected to UV ozone treatment for 370 seconds.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that the surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed by a vacuum evaporation method.

After reducing the pressure of the vacuum evaporation apparatus to $10^{-4}$ Pa, 4,4'-di(N-carbazolyl)biphenyl (abbreviation: CBP) and molybdenum(VI) oxide were co-evaporated with a mass ratio of CBP (abbreviation) to molybdenum oxide being 4:2, whereby the hole-injection layer 1111 was formed over the first electrode 1101. The thickness of the hole-injection layer 1111 was 60 nm. Note that the co-evaporation is an evaporation method in which some different substances are evaporated from some different evaporation sources at the same time.

Then, 1,3-bis(N-carbazolyl)benzene (abbreviation: mCP) was deposited by evaporation to a thickness of 20 nm, so that the hole-transport layer 1112 was formed.

Next, the light-emitting layer 1113 was formed over the hole-transport layer 1112 in the following manner. First, 3-[3,6-di(9H-carbazol-9-yl)-9H-carbazol-9-yl]pyridine (abbreviation: Cz2CzPy) and tris[3-methyl-1-(2-methylphenyl)-5-phenyl-1H-1,2,4-triazolato]iridium(III) (abbreviation: [Ir(Mptzl-mp)₃]) were co-evaporated with a mass ratio of Cz2CzPy (abbreviation) to [Ir(Mptzl-mp)₃] (abbreviation) being 1:0.08 to form a 30-nm-thick film. Then, 2-[3-(dibenzothiophen-4-yl)phenyl]-1-phenyl-1H-benzimidazole (abbreviation: mDBTBIm-II) and [Ir(Mptzl-mp)₃] (abbreviation) were co-evaporated with a mass ratio of mDBTBIm-II (abbreviation) to [Ir(Mptzl-mp)₃] (abbreviation) being 1:0.08 to form a 10-nm-thick film. Thus, the light-emitting layer 1113 having a stacked structure was formed.

Then, bathophenanthroline (abbreviation: Bphen) was deposited by evaporation to a thickness of 15 nm over the light-emitting layer 1113, whereby the electron-transport layer 1114 was formed. Furthermore, lithium fluoride was then deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, Light-emitting Element 2 was obtained. Note that in all the above evaporation steps, evaporation was performed by a resistance-heating method.

Comparative Light-emitting Element 2 was fabricated for comparison with Light-emitting Element 2. Comparative Light-emitting Element 2 was fabricated in a similar manner to that of Light-emitting Element 2 except that the first layer of the light-emitting layer which was on and in contact with the hole-transport layer 1112 was formed to a thickness of 30 nm by co-evaporation of 3,6-di(9H-carbazol-9-yl)-9-phenyl-9H-carbazole (abbreviation: PhCzGI) and tris[3-methyl-1-(2-methylphenyl)-5-phenyl-1H-1,2,4-triazolato]iridium(III) (abbreviation: [Ir(Mptzl-mp)₃]) with a mass ratio of PhCzGI (abbreviation) to [Ir(Mptzl-mp)₃] (abbreviation) being 1:0.08.

Element structures of Light-emitting Element 2 and Comparative Light-emitting Element 2 obtained as described above are shown in Table 3.

TABLE 3

|  | First Electrode | Hole-injection Layer | Hole-transport Layer | Light-emitting Layer | | Electron-transport Layer | Electron-injection Layer | Second Electrode |
| --- | --- | --- | --- | --- | --- | --- | --- | --- |
| Light-emitting Element 2 | ITSO (110 nm) | CBP:MoOx (4:2 60 nm) | mCP (20 nm) | * | ** | Bphen (15 nm) | LiF (1 nm) | Al (200 nm) |
| Comparative Light-emitting Element 2 | ITSO (110 nm) | CBP:MoOx (4:2 60 nm) | mCP (20 nm) | *** | **** | Bphen (15 nm) | LiF (1 nm) | Al (200 nm) |

\* Cz2CzPy: [Ir(Mptz1-mp)$_3$] (1:0.08 30 nm)
\*\* mDBTBImII: [Ir(Mptz1-mp)$_3$] (1:0.08 10 nm)
\*\*\* PhCzGI: [Ir(Mptz1-mp)$_3$] (1:0.08 30 nm)
\*\*\*\* mDBTBImII: [Ir(Mptz1-mp)$_3$] (1:0.08 10 nm)

Further, after fabrication, each of Light-emitting Element 2 and Comparative Light-emitting Element 2 was sealed in a glove box containing a nitrogen atmosphere so as not to be exposed to the air (specifically, a sealant was applied onto an outer edge of the element and heat treatment was performed at 80° C. for 1 hour at the time of sealing).

Operation Characteristics of Light-Emitting Element 2 and Comparative Light-Emitting Element 2

Operation characteristics of the fabricated Light-emitting Element 2 and Comparative Light-emitting Element 2 were measured. Note that the measurement was carried out at room temperature (under an atmosphere in which the temperature was kept at 25° C.).

Figure 16:
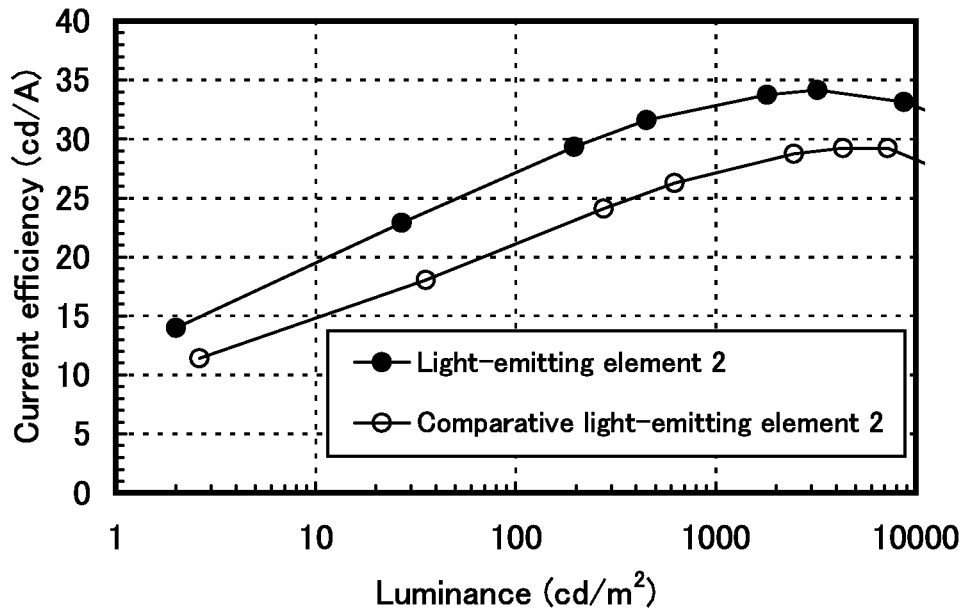
FIG. 16 shows luminance-current efficiency characteristics of Light-emitting Element 2 and Comparative Light-emitting Element 2.
Figure 17:
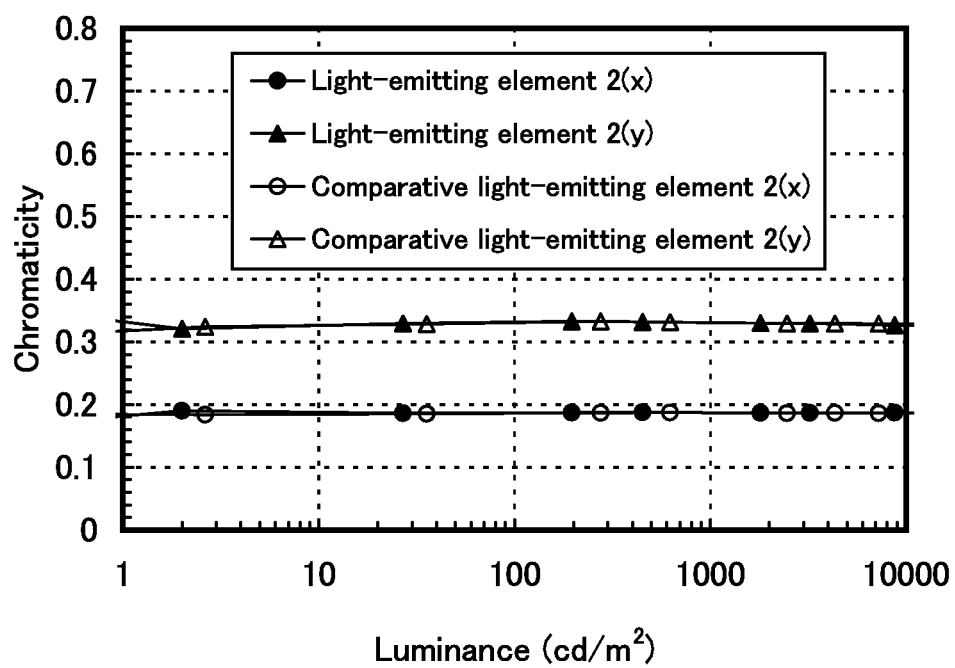
FIG. 17 shows luminance-chromaticity characteristics of Light-emitting Element 2 and Comparative Light-emitting Element 2.
Figure 18:
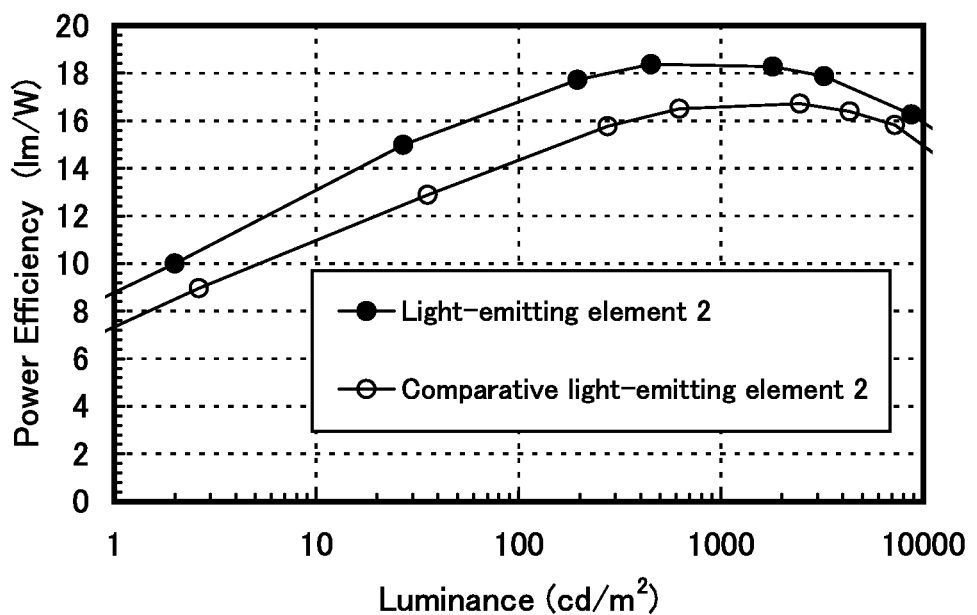
FIG. 18 shows luminance-power efficiency characteristics of Light-emitting Element 2 and Comparative Light-emitting Element 2.

The luminance-current efficiency characteristics of Light-emitting Element 2 and Comparative Light-emitting Element 2 are shown in FIG. 16. The luminance-chromaticity characteristics of Light-emitting Element 2 and Comparative Light-emitting Element 2 are shown in FIG. 17. The luminance-power efficiency characteristics of Light-emitting Element 2 and Comparative Light-emitting Element 2 are shown in FIG. 18.

FIG. 16 shows that Light-emitting Element 2 in which 3-[3,6-di(9H-carbazol-9-yl)-9H-carbazol-9-yl]pyridine (abbreviation: Cz2CzPy), one embodiment of the carbazole compound of the present invention, is used in the hole-transport layer and in part of the light-emitting layer as a host material has low power consumption and high efficiency. FIG. 17 shows that Light-emitting Element 2 has favorable carrier balance at any luminance.

Table 4 below shows initial values of main characteristics of Light-emitting Element 2 and Comparative Light-emitting Element 2 at a luminance of about 1000 cd/m$^2$.

peak at around 470 nm and it was indicated that the emission spectra were derived from emission of [Ir(Mptzl-mp)$_3$] (abbreviation) included in the light-emitting layer 1113.

The above results showed that 3-[3,6-di(9H-carbazol-9-yl)-9H-carbazol-9-yl]pyridine (abbreviation: Cz2CzPy), which is one embodiment of the carbazole compound of the present invention, has a high T$_1$ level and can be used for a host material or a carrier-transport material in an element that emits phosphorescence (or fluorescence) in the visible region (having a longer wavelength than blue color).

As described above, since the carbazole compound of the present invention has a carbazole skeleton and a pyridine skeleton, which are respectively a hole-transport skeleton and an electron-transport skeleton, the carbazole compound favorably transports both types of carriers, holes and electrons. Therefore, when used as a host material in a light-emitting layer, the carbazole compound can favorably inject carriers to a dopant material, which is a light-emitting material. In addition, higher emission efficiency can be achieved by, as in Light-emitting Element 2 in this example, using the carbazole compound of the present invention for the light-emitting layer (the above-mentioned first layer of the light-emitting layer) which is in contact with the hole-transport layer, and using a material (e.g., mCP (abbreviation)) whose LUMO level is higher than that of the carbazole compound of the present invention for the hole-transport layer. The reason for this is conceivably blocking of electrons at the first layer of the light-emitting layer (or near the interface between the first layer of the light-emitting layer and the hole-transport layer). Furthermore, the emission efficiency can be increased by, as in Light-emitting Element 2 in this example, using the carbazole compound of the present invention for the light-emitting

TABLE 4

|  | Voltage (V) | Current (mA) | Current Density (mA/cm$^2$) | Chromaticity (x, y) | Luminance (cd/m$^2$) | Current Efficiency (cd/A) | Power Efficiency (lm/W) |
| --- | --- | --- | --- | --- | --- | --- | --- |
| Light-emitting Element 2 | 5.4 | 0.057 | 1.4 | (0.19, 0.33) | 450 | 32 | 18 |
| Comparative Light-emitting Element 2 | 5.0 | 0.095 | 2.4 | (0.19, 0.33) | 620 | 26 | 17 |

The above results in Table 4 also show that Light-emitting Element 2 fabricated in this example has high luminance and high current efficiency.

Figure 19:
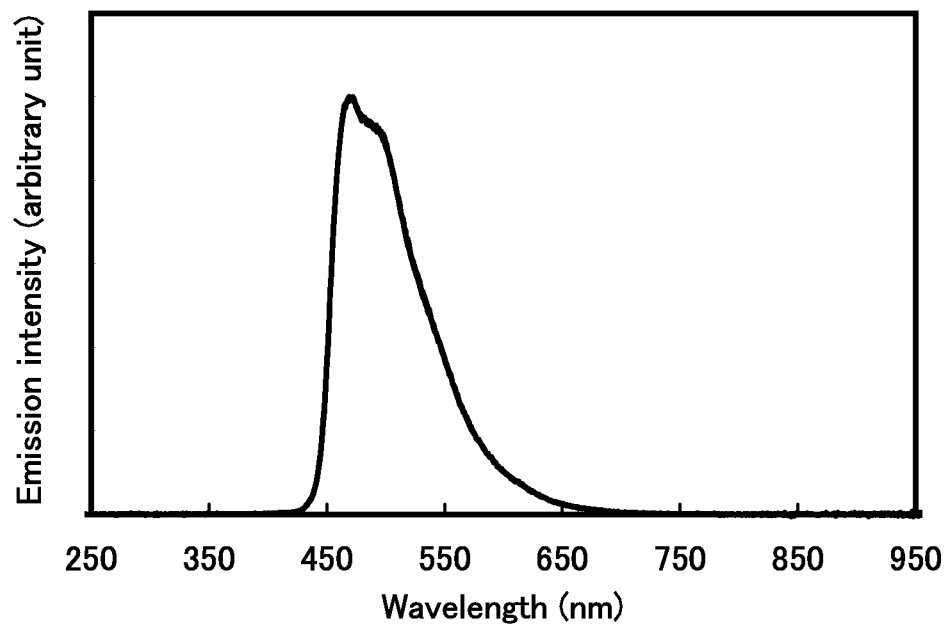
FIG. 19 shows emission spectra of Light-emitting Element 2 and Comparative Light-emitting Element 2.

FIG. 19 shows emission spectra when a current at a current density of 2.5 mA/cm$^2$ was supplied to Light-emitting Element 2 and Comparative Light-emitting Element 2. As shown in FIG. 19, each of the emission spectra of Light-emitting Element 2 and Comparative Light-emitting Element 2 has a layer (the above-mentioned first layer of the light-emitting layer) which is in contact with the hole-transport layer, and using a material (e.g., mDBTBIm-II (abbreviation)) whose HOMO level is lower than that of the carbazole compound of the present invention for the light-emitting layer (the above-mentioned second layer of the light-emitting layer) which is in contact with the first layer of the light-emitting layer and the electron-transport layer. The reason for this is conceivably blocking of holes at the second layer of the light-emitting layer (or near the interface between the second layer of the light-emitting layer and the electron-transport layer).

Figure 20:
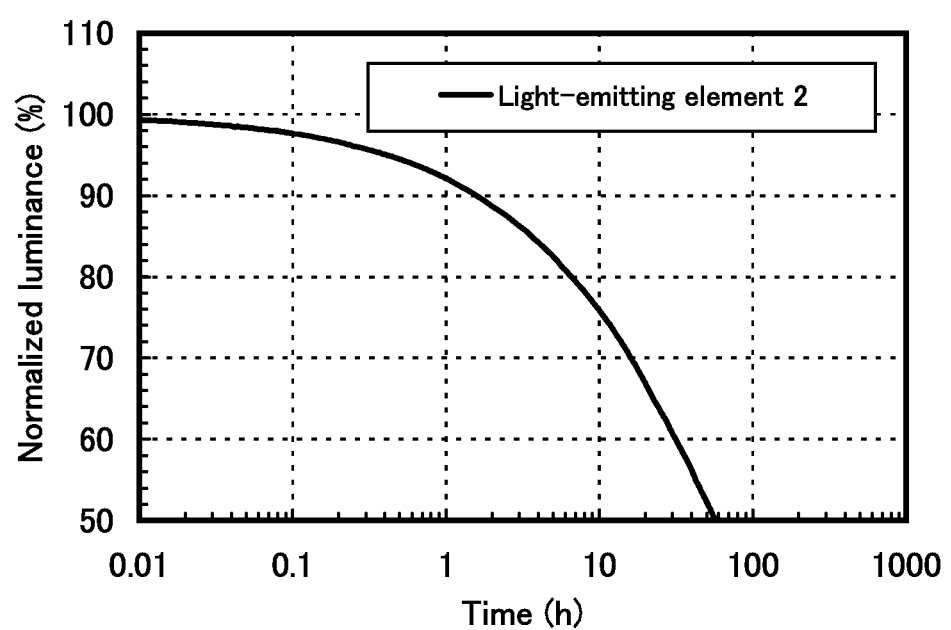
FIG. 20 shows reliability of Light-emitting Element 2.

Light-emitting Element 2 was subjected to a reliability test. Results of the reliability test are shown in FIG. 20. In FIG. 20, the vertical axis represents normalized luminance (%) with an initial luminance of 100% and the horizontal axis represents driving time (h) of the element. Note that in the reliability test, Light-emitting Element 2 was driven under the conditions where the initial luminance was set to 300 cd/m² and the current density was constant. Light-emitting Element 2 kept 60% of the initial luminance after 30 hours elapsed. This indicates high reliability of Light-emitting Element 2, in which part of the light-emitting layer includes Cz2CzPy (abbreviation), one embodiment of the carbazole compound of the present invention, as the host material. In addition, it was confirmed that with the use of the carbazole compound of the present invention, a light-emitting element with a long lifetime can be obtained.

Reference Synthesis Example 1

A method of synthesizing tris[3-methyl-1-(2-methylphenyl)-5-phenyl-1H-1,2,4-triazolato]iridium(III) (abbreviation: [Ir(Mptzl-mp)₃]), which was used in Examples 2 and 3 above, will be specifically described. A structure of [Ir(Mptzl-mp)₃] is shown below.

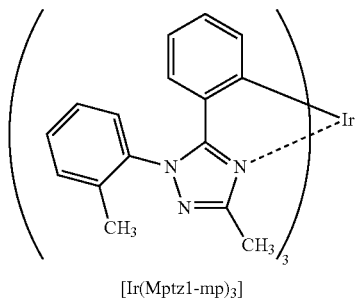

[Ir(Mptzl-mp)₃]

Step 1: Synthesis of N-(1-Ethoxyethylidene)benzamide

First, 15.5 g of ethyl acetimidate hydrochloride, 150 mL of toluene, and 31.9 g of triethylamine (Et₃N) were put into a 500-mL three-neck flask and the mixture was stirred at room temperature for 10 minutes. With a 50-mL dropping funnel, a mixed solution of 17.7 g of benzoyl chloride and 30 mL of toluene was added dropwise to this mixture, and the mixture was stirred at room temperature for 24 hours. After a predetermined time elapsed, the reaction mixture was suction-filtered, and the solid was washed with toluene. The obtained filtrate was concentrated to give N-(1-ethoxyethylidene)benzamide (a red oily substance, 82% yield). A synthesis scheme of Step 1 is shown in (a-1) below.

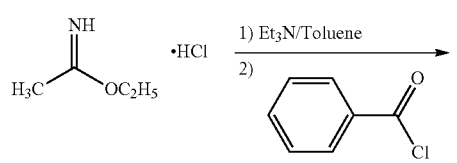

(a-1)

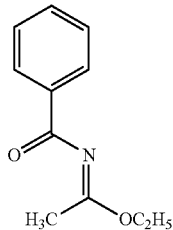

Step 2: Synthesis of 3-Methyl-1-(2-methylphenyl)-5-phenyl-1H-1,2,4-triazole (Abbreviation: HMptzl-mp)

Next, into a 300-mL recovery flask were put 8.68 g of o-tolylhydrazine hydrochloride, 100 mL of carbon tetrachloride, and 35 mL of triethylamine (Et₃N), and the mixture was stirred at room temperature for 1 hour. After a predetermined time elapsed, 8.72 g of N-(1-ethoxyethylidene)benzamide obtained in Step 1 above was added to this mixture, and the mixture was stirred at room temperature for 24 hours. After a predetermined time elapsed, water was added to the reaction mixture, and the aqueous layer was subjected to extraction with chloroform. The organic layer was washed with saturated brine, and dried with anhydrous magnesium sulfate added thereto. The obtained mixture was gravity-filtered, and the filtrate was concentrated to give an oily substance. The obtained oily substance was purified by silica gel column chromatography. Dichloromethane was used as a developing solvent. The obtained fraction was concentrated to give 3-methyl-1-(2-methylphenyl)-5-phenyl-1H-1,2,4-triazole (abbreviation: HMptzl-mp) (an orange oily substance, 84% yield). A synthesis scheme of Step 2 is shown in (a-2) below

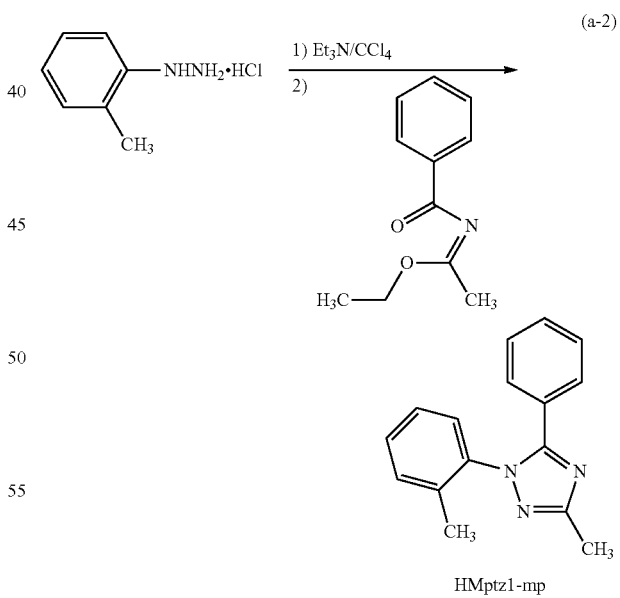

(a-2)

HMptzl-mp

Step 3: Synthesis of Tris[3-methyl-1-(2-methylphenyl)-5-phenyl-1H-1,2,4-triazolato]iridium(III) (Abbreviation: [Ir(Mptzl-mp)₃])

Next, 2.71 g of the ligand HMptzl-mp obtained in Step 2 above and 1.06 g of tris(acetylacetonato)iridium(III) were put into a reaction container provided with a three-way cock. The air in this reaction container was replaced with argon, and heated at 250° C. for 48 hours to cause a reaction. This reaction mixture was dissolved in dichloromethane and purified by silica gel column chromatography. As the developing solvent, dichloromethane was first used, and a mixed solvent of dichloromethane and ethyl acetate in a ratio of 10:1 (v/v) was then used. The obtained fraction was concentrated to give a solid. This solid was washed with ethyl acetate, and recrystallized from a mixed solvent of dichloromethane and ethyl acetate to give the organometallic complex [Ir(Mptzl-mp)$_3$], which is one embodiment of the present invention (a yellow powder, 35% yield). A synthesis scheme of Step 3 is shown in (a-3) below.

(a-3)

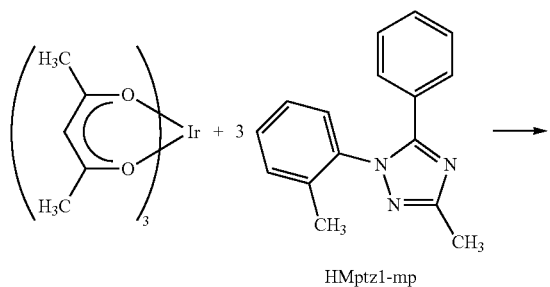

HMptz1-mp

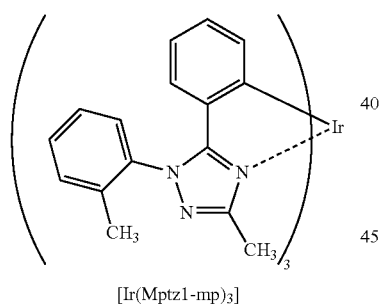

[Ir(Mptz1-mp)$_3$]

An analysis result by nuclear magnetic resonance spectrometry ($^1$H NMR) of the yellow powder obtained in Step 3 above is shown below. The results showed that the above-described organometallic complex [Ir(Mptzl-mp)$_3$] was obtained.

$^1$H NMR data of the obtained substance are as follows:

$^1$H NMR (CDCl$_3$, 300 MHz): δ (ppm)=1.94-2.21 (m, 18H), 6.47-6.76 (m, 12H), 7.29-7.52 (m, 12H).

Reference Synthesis Example 2

A method of synthesizing 3,6-di(9H-carbazol-9-yl)-9-phenyl-9H-carbazole (abbreviation: PhCzGI), which was used in Examples 2 and 3 above, will be specifically described. A structure of PhCzGI (abbreviation) is shown below.

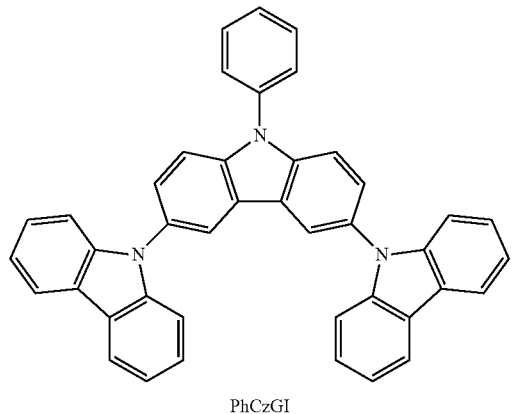 [SMILES: c1ccc(-n2c3ccc(-n4c5ccccc5c5ccccc54)cc3c3cc(-n4c5ccccc5c5ccccc54)ccc32)cc1]

PhCzGI

Synthesis of 3,6-Di(9H-carbazol-9-yl)-9-phenyl-9H-carbazole (Abbreviation: PhCzGI)

First, in a 200-mL three-neck flask, a mixture including 2.8 g (7.0 mmol) of 3,6-dibromo-9-phenyl-9H-carbazole, 2.7 g (16 mmol) of carbazole, 1.9 g (10 mmol) of copper(I) iodide, 2.5 g (10 mmol) of 18-crown-6-ether, 2.8 g (20 mmol) of potassium carbonate, and 20 mL of 1,3-dimethyl-3,4,5,6-tetrahydro-2(1H)-pyrimidinone (abbreviation: DMPU) was stirred under a nitrogen atmosphere at 180° C. for 3.5 hours to cause a reaction.

After the reaction, water was added to this reaction mixture and filtration was performed. Methanol was added to an obtained residue and ultrasonic cleaning was performed. The residue was collected and dried; then, toluene was added and the mixture was stirred while being heated, and then filtered. An obtained filtrate was purified by silica gel column chromatography. An obtained fraction was recrystallized, so that an objective substance was obtained as 1.5 g of white powder at a yield of 38%. The above reaction is shown in Scheme (b-1) below.

(b-1)

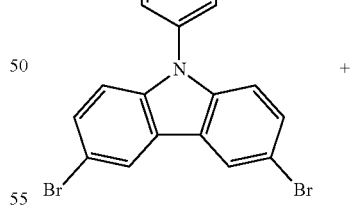

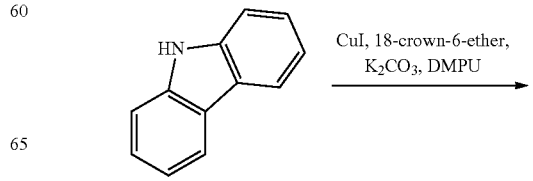

-continued

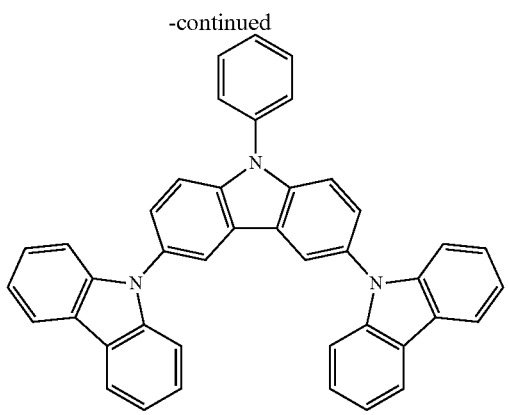

The Rf values of the objective substance, 3,6-dibromo-9-phenyl-9H-carbazole, and carbazole were respectively 0.32, 0.73, and 0.18 which were obtained by silica gel thin layer chromatography (TLC) (with a developing solvent containing ethyl acetate and hexane in a 1:10 ratio).

Analysis results by nuclear magnetic resonance spectrometry ($^1$H NMR) of the compound obtained by the above synthesis method are shown below. The results showed that the above-described PhCzGI (abbreviation) was obtained.

$^1$H NMR data of the obtained substance are as follows:
$^1$H NMR (CDCl$_3$, 300 MHz): δ (ppm)=7.26-7.32 (m, 4H), 7.40 (d, J=3.3 Hz, 8H), 7.57-7.74 (m, 9H), 8.16 (d, J=7.5 Hz, 4H), 8.28 (d, J=1.5 Hz, 2H).

Example 4

Synthesis Example 2

In this example, a method of synthesizing 3-{3-[3,6-di-(9H-carbazol-9-yl)-9H-carbazol-9-yl]phenyl}pyridine (abbreviation: mCz2CzPPy), which is one embodiment of the carbazole compound of the present invention represented by Structural Formula (101) in Embodiment 1, is described. The structure of mCz2CzPPy (abbreviation) is shown below.

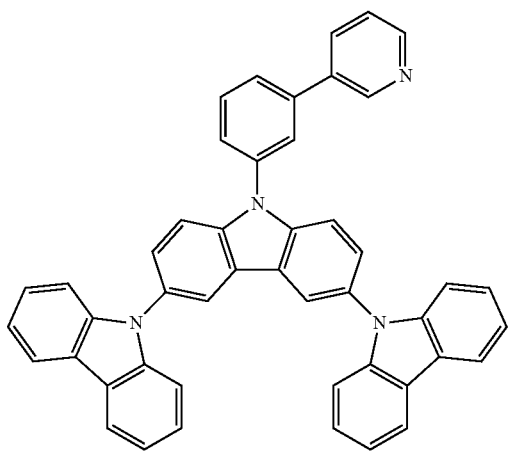

(101)

Synthesis of 3-[3-(3,6-Dibromo-9H-carbazol-9-yl)phenyl]pyridine (Abbreviation: Cz2CzPPy)

Into a 200-ml recovery flask were put 1.3 g (3.96 mmol) of 3-[3-(9H-carbazol-9-yl-phenyl)]pyridine, 0.71 g (4.0 mmol) of N-bromosuccinimide (abbreviation: NBS), and 50 ml of ethyl acetate, and the mixture was stirred for 51 hours. After the mixture was stirred for the predetermined time, 0.71 g (4.0 mmol) of N-bromosuccinimide (abbreviation: NBS) was added and the mixture was stirred for 45 hours. After the reaction, water was added and the mixture was stirred; then, filtration was performed. Water was added to an obtained residue and irradiation with ultrasonic waves was performed. The mixture was filtered to give a residue. The obtained solid was dried and an objective substance was obtained as 1.5 g of a white solid at a yield of 81%.

A synthesis scheme of the above synthesis method is illustrated in (B-1) below.

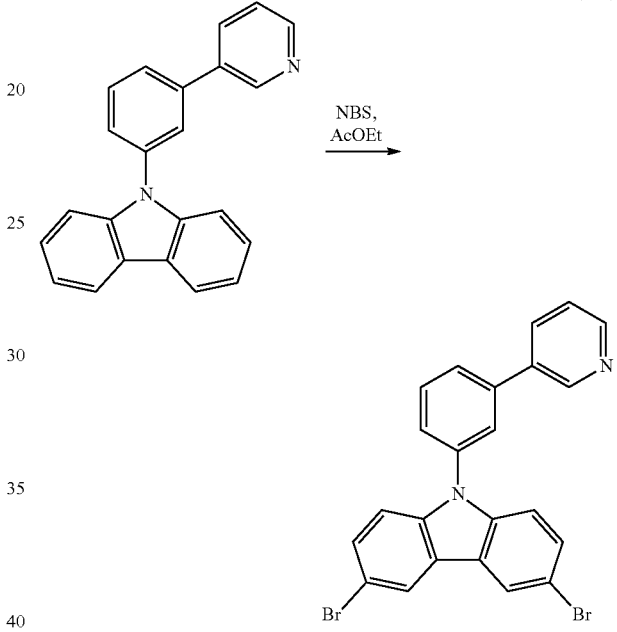

(B-1)

Synthesis of 3-{3-[3,6-Di-(9H-carbazol-9-yl)-9H-carbazol-9-yl]phenyl}pyridine (Abbreviation: mCz2CzPPy)

Into a 100-ml three-neck flask were put 0.9 g (1.9 mmol) of 3-[3-(3,6-dibromo-9H-carbazol-9-yl)phenyl]pyridine, 700 mg (4.2 mmol) of carbazole, 1.2 g (8.4 mmol) of potassium carbonate, 110 mg (0.421 mmol) of 18-crown-6-ether, and about 3 ml of 1,3-dimethyl-3,4,5,6-tetrahydro-2(1H)-pyrimidinone (abbreviation: DMPU), and the mixture was degassed by being stirred under a reduced pressure. To this mixture was added 80 mg (0.42 mmol) of copper(I) iodide, and the mixture was stirred at 180° C. for 24 hours under a nitrogen stream. After the mixture was stirred for the predetermined time, water was added to the mixture and suction filtration was performed. An obtained residue was put in filter paper to be dried. The residue was added to toluene, and the mixture was heated and was then filtered through Celite.

An obtained filtrate was purified by silica gel column chromatography (purification with a mixed solution of toluene and chloroform was followed by purification with a mixed solution of hexane and toluene) to give a brown solid. A mixed solution of methanol and acetone was added to the brown solid and irradiation with ultrasonic waves was performed, so that the brown solid was suspended. The suspension was suction-filtered to give a pale brown solid. The pale brown solid was purified by silica gel column chromatography (hexane:toluene=1:1) to give a pale brown solid. Ethyl acetate was added to the pale brown solid and irradiation with ultrasonic waves was performed, so that the pale brown solid was suspended. Then, suction filtration was performed to give a white solid. Hexane was added to the white solid and irradiation with ultrasonic waves was performed, so that the white solid was suspended. Suction filtration was then performed to give 390 mg of a white solid, which was an objective substance, at a yield of 32%.

A synthesis scheme of the above synthesis method is illustrated in (B-2) below.

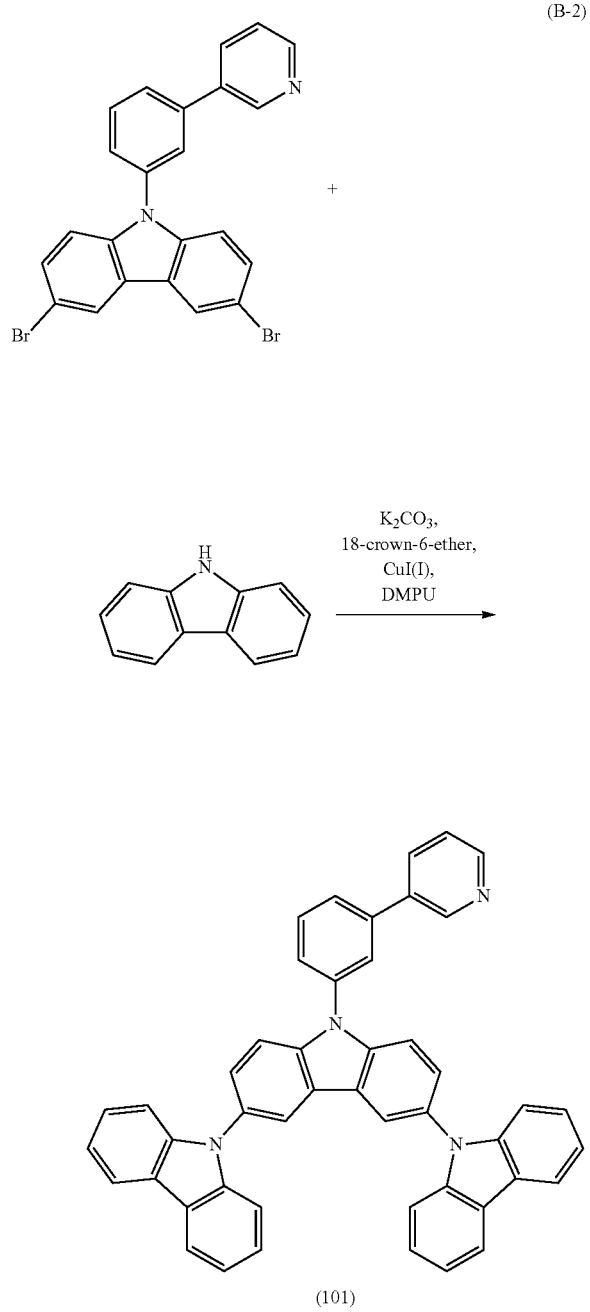

Figure 21A:
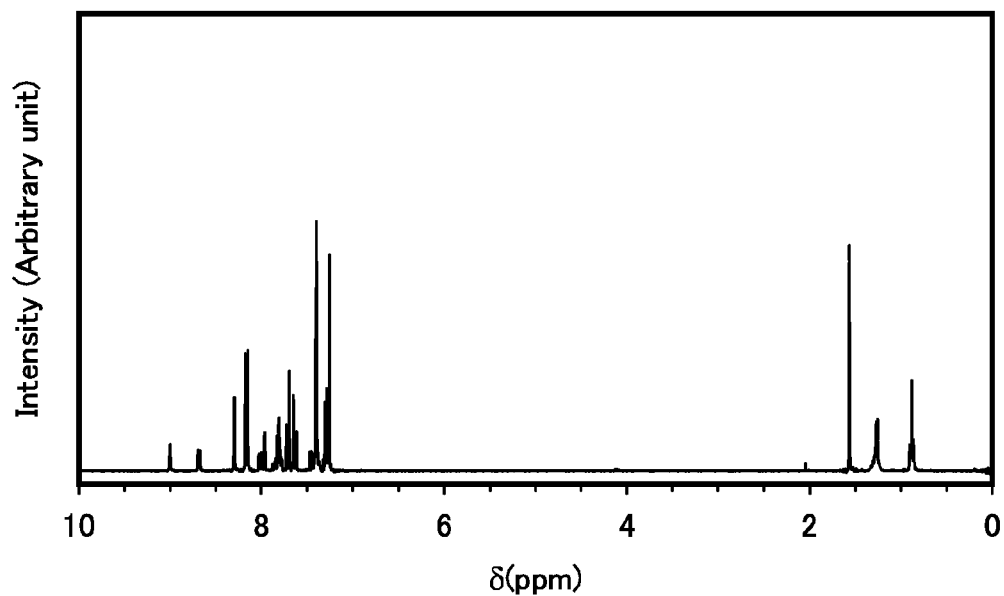
FIGS. 21A and 21B show $^1$H NMR charts of a carbazole compound represented by Structural Formula (101)
Figure 21B:
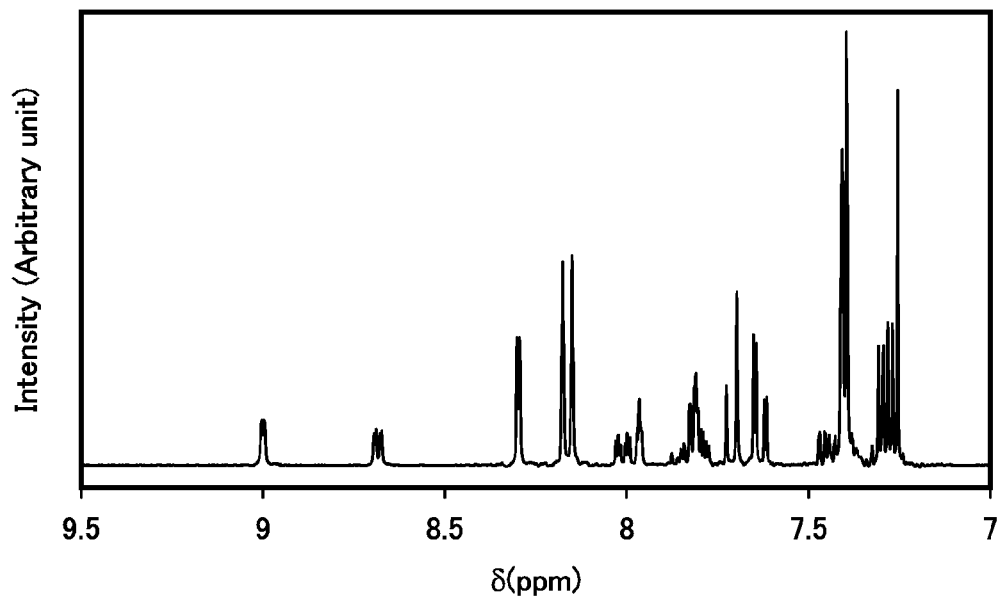

An analysis result by nuclear magnetic resonance spectrometry ($^1$H NMR) of the compound obtained by the above synthesis method is shown below. The $^1$H NMR charts are shown in FIGS. 21A and 21B. Note that FIG. 21B is an enlarged chart of FIG. 21A. The result revealed that 3-{3-[3,6-di-(9H-carbazol-9-yl)-9H-carbazol-9-yl]phenyl}pyridine (abbreviation: mCz2CzPPy), which is one embodiment of the carbazole compound of the present invention represented by Structural Formula (101) above, was obtained.

$^1$H NMR (CDCl$_3$, 300 MHz): δ (ppm)=7.27-7.31 (m, 4H), 7.38-7.47 (m, 9H), 7.63 (dd, J=8.7 Hz, J=2.1 Hz, 2H), 7.71 (d, J=9.0 Hz, 2H), 7.78-7.84 (m, 3H), 7.96-8.03 (m, 2H), 8.16 (d, J=7.8 Hz, 4H), 8.30 (d, J=2.1 Hz, 2H), 8.68 (dd, J=4.8 Hz, J=1.5 Hz, 1H), 9.0 (d, J=1.5 Hz, 1H).

The results of the measurement of a thin film of mCz2CzPPy (abbreviation) with a photoelectron spectrometer (AC-2, manufactured by Riken Keiki Co., Ltd.) in the air indicated that the HOMO level of mCz2CzPPy is −5.62 eV. The Tauc plot of the absorption spectrum of the thin film revealed that the absorption edge is 3.14 eV. Thus, the energy gap in the solid state was estimated to be 3.14 eV, which means that the LUMO level of mCz2CzPPy is −2.48 eV.

Thus, it was found that the HOMO level of mCz2CzPPy (abbreviation) is relatively low and the LUMO level thereof is high, which shows that mCz2CzPPy has a wide band gap (Bg).

Further, the HOMO level and the LUMO level of mCz2CzPPy (abbreviation) were obtained by cyclic voltammetry (CV) measurement. An electrochemical analyzer (ALS model 600A or 600C, manufactured by BAS Inc.) was used for the CV measurement.

On the assumption that the intermediate potential (the half-wave potential) between the oxidation peak potential $E_{pa}$ and the reduction peak potential $E_{pc}$ which are obtained in the CV measurement corresponds to the HOMO level, the HOMO level of mCz2CzPPy (abbreviation) was calculated to be −5.75 eV, and the LUMO level of mCz2CzPPy (abbreviation) was calculated to be −2.31 eV.

Thus, the carbazole compound of the present invention was found to have a relatively low HOMO level and a high LUMO level, which means the carbazole compound has a wide band gap (Bg). It is preferable that a host material of a light-emitting layer have a HOMO level equal to or deeper than that of a light-emitting material and have a LUMO level equal to or shallower than that of the light-emitting material. Accordingly, the carbazole compound of the present invention can be used favorably as a host material in a light-emitting layer. Specifically, it was found that the carbazole compound of the present invention is favorable as a host material for a pyridine-based light-emitting material (a material in which iridium is bonded to a pyridine skeleton to form an ortho-metalated structure), e.g., [Ir(ppy)$_2$(acac)] (abbreviation) whose HOMO level and LUMO level are respectively −5.41 eV and −2.39 eV, or [Ir(ppy)$_3$] (abbreviation) whose HOMO level and LUMO level are respectively −5.32 eV and −2.29 eV (these HOMO and LUMO levels were obtained by CV measurement).

This application is based on Japanese Patent Application serial no. 2011-178966 filed with Japan Patent Office on Aug. 18, 2011 and Japanese Patent Application serial no. 2012-135953 filed with Japan Patent Office on Jun. 15, 2012, the entire contents of which are hereby incorporated by reference.

What is claimed is:

1. A carbazole compound represented by General Formula (G3),

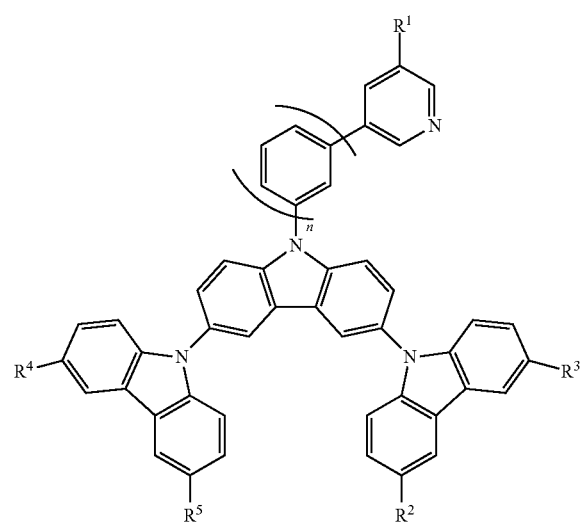

(G3)

wherein, in the formula:
R¹ to R⁵ each independently represent any of hydrogen, an unsubstituted phenyl group, and an unsubstituted biphenyl group; and
n is 0.

2. A carbazole compound represented by General Formula (G4),

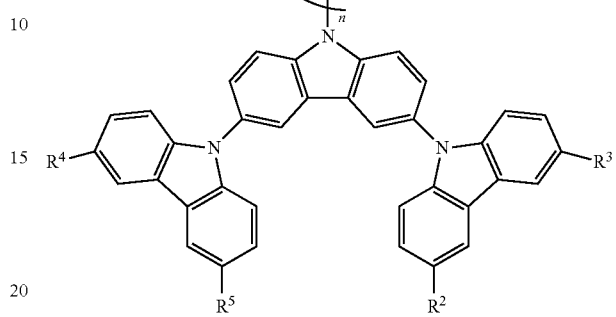

(G4)

wherein, in the formula:
R² to R⁵ each independently represent any of hydrogen, an unsubstituted phenyl group, and an unsubstituted biphenyl group; and
n is 0.

3. A carbazole compound represented by Structural Formula (100)

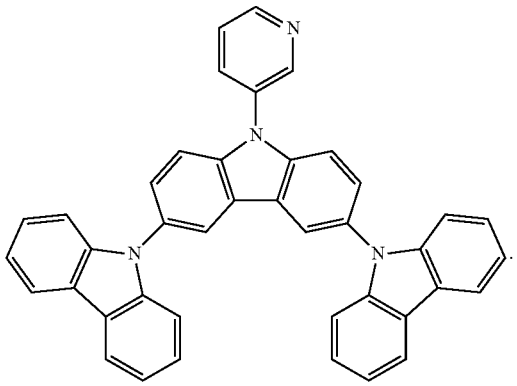

(100)

* * * * *

UNITED STATES PATENT AND TRADEMARK OFFICE
CERTIFICATE OF CORRECTION

PATENT NO. : 9,029,558 B2
APPLICATION NO. : 13/570367
DATED : May 12, 2015
INVENTOR(S) : Harue Osaka et al.

It is certified that error appears in the above-identified patent and that said Letters Patent is hereby corrected as shown below:

In the Specification:

Col. 8, line 34, "by a in General" should read --by α in General--

Col. 21, lines 38-39, "diphenyl-N,N,N'N'-tetrakis" should read --diphenyl-N,N,N',N'-tetrakis--

Col. 22, line 65, "$C_ZAlPA$" should read --$C_zA1PA$--

Col. 23, line 62, "1,3-bis[5-(4-tert" should read --1,3-bis[5-(p-tert--

Col. 27, lines 31-32, "[4,5-α]thienyp-pyridinato" should read --[4,5-α]thienyl)pyridinato--

Col. 27, line 55, "7mDBTPDB-q-II" should read --7mDBTPDBq-II--

Col. 32, line 4, "layer (G) 4040" should read --layer (G) 404G--

Col. 32, line 30, "404G and" should read --404G, and--

Col. 32, line 58, "410G respectively," should read --410G, respectively,--

Col. 33, line 66, "404R However," should read --404R. However,--

Col. 34, line 7, "410G the" should read --410G, the--

Col. 34, line 17, "404G Therefore," should read --404G. Therefore--

Col. 41, line 46, "G2 T of MS" should read --G2 Tof MS--

Col. 46, line 10, "$(Mptzl-mp)_3$" should read --$(Mptz1-mp)_3$--

Col. 46, line 11, "$(Mptzl-mp)_3$" should read --$(Mptz1-mp)_3$--

Col. 46, line 14, "$(Mptzl-mp)_3$" should read --$(Mptz1-mp)_3$--

Col. 46, line 16, "$(Mptzl-mp)_3$" should read --$(Mptz1-mp)_3$--

Col. 46, line 43, "$(Mptzl-mp)_3$" should read --$(Mptz1-mp)_3$--

Col. 46, line 44, "$(Mptzl-mp)_3$" should read --$(Mptz1-mp)_3$--

Col. 47, line 57, "$(Mptzl-mp)_3$" should read --$(Mptz1-mp)_3$--

Col. 50, line 28, "$(Mptzl-mp)_3$" should read --$(Mptz1-mp)_3$--

Col. 50, line 29, "$(Mptzl-mp)_3$" should read --$(Mptz1-mp)_3$--

Signed and Sealed this
Fifth Day of January, 2016

Michelle K. Lee
*Director of the United States Patent and Trademark Office*

CERTIFICATE OF CORRECTION (continued)
U.S. Pat. No. 9,029,558 B2

In the Specification:

Col. 50, line 32, "(Mptzl-mp)$_3$" should read --(Mptz1-mp)$_3$--

Col. 50, line 34, "(Mptzl-mp)$_3$" should read --(Mptz1-mp)$_3$--

Col. 50, line 62, "(Mptzl-mp)$_3$" should read --(Mptz1-mp)$_3$--

Col. 50, line 63, "(Mptzl-mp)$_3$" should read --(Mptz1-mp)$_3$--

Col. 52, line 16, "(Mptzl-mp)$_3$" should read --(Mptz1-mp)$_3$--

Col. 53, line 25, "(Mptzl-mp)$_3$" should read --(Mptz1-mp)$_3$--

Col. 53, line 26, "(Mptzl-mp)$_3$" should read --(Mptz1-mp)$_3$--

Col. 54, line 14, "HMptzl" should read --HMptz1--

Col. 54, line 33, "HMptzl-mp" should read --HMptz1-mp--

Col. 54, line 34, "(a-2) below" should read --(a-2) below.--

Col. 54, line 64, "(Mptzl-mp)$_3$" should read --(Mptz1-mp)$_3$--

Col. 54, line 66, "HMptzl-mp" should read --HMptz1-mp--

Col. 55, line 11, "(Mptzl-mp)$_3$" should read --(Mptz1-mp)$_3$--

Col. 55, line 54, "(Mptzl-mp)$_3$" should read --(Mptz1-mp)$_3$--

In the Claims:

Col. 62, line 27, claim 3, "(100)" should read --(100).--